US012586671B1

(12) United States Patent
Khaziran

(10) Patent No.: US 12,586,671 B1
(45) Date of Patent: Mar. 24, 2026

(54) SYSTEMS AND METHODS FOR ANATOMICAL AND INJURY MODELING

(71) Applicant: Sports Rehab LA, Encino, CA (US)

(72) Inventor: Patrick Khaziran, Valencia, CA (US)

(73) Assignee: Sports Rehab LA, Encino, CA (US)

( * ) Notice: Subject to any disclaimer, the term of this patent is extended or adjusted under 35 U.S.C. 154(b) by 0 days.

(21) Appl. No.: 18/949,668

(22) Filed: Nov. 15, 2024

(51) Int. Cl.
*G16H 20/30* (2018.01)
*G16H 50/30* (2018.01)

(52) U.S. Cl.
CPC ............. *G16H 20/30* (2018.01); *G16H 50/30* (2018.01)

(58) Field of Classification Search
CPC ............................... G16H 20/30; G16H 50/30
See application file for complete search history.

(56) References Cited

U.S. PATENT DOCUMENTS

| | | | | |
|---|---|---|---|---|
| 2009/0063194 A1* | 3/2009 | Rosneck | ................ | G16H 40/63 705/3 |
| 2016/0078708 A1* | 3/2016 | Salem | ................ | G07F 17/0092 221/199 |
| 2019/0066832 A1* | 2/2019 | Kang | .................... | A61B 5/1128 |
| 2019/0371449 A1* | 12/2019 | Rindal | .................... | G16H 20/30 |
| 2020/0237291 A1* | 7/2020 | Sundaram | ............. | A61B 5/4528 |
| 2021/0217508 A1* | 7/2021 | Kosofsky | ............... | G16H 10/60 |
| 2022/0117544 A1* | 4/2022 | Stavros | ................ | A61B 5/7435 |

FOREIGN PATENT DOCUMENTS

WO    WO-2023127015 A1 *    7/2023    ............. A61B 5/112

\* cited by examiner

*Primary Examiner* — Kambiz Abdi
*Assistant Examiner* — Tran N Nguyen
(74) *Attorney, Agent, or Firm* — Foley & Lardner LLP

(57)    ABSTRACT

The present disclosure relates to systems and methods for anatomical and injury modeling. A system can process multimedia and sensor data collected during various anatomical tests, such as mobility tests and muscle, ligament, or tendon assessments, performed by a user. By applying this data to neural network models, the system can generate anatomy scores and subscores for specific body regions, identifying potential vulnerabilities in the anatomy of the user. The system can further generate a personalized conditioning protocol to address these vulnerabilities and reducing the likelihood of injury.

16 Claims, 7 Drawing Sheets

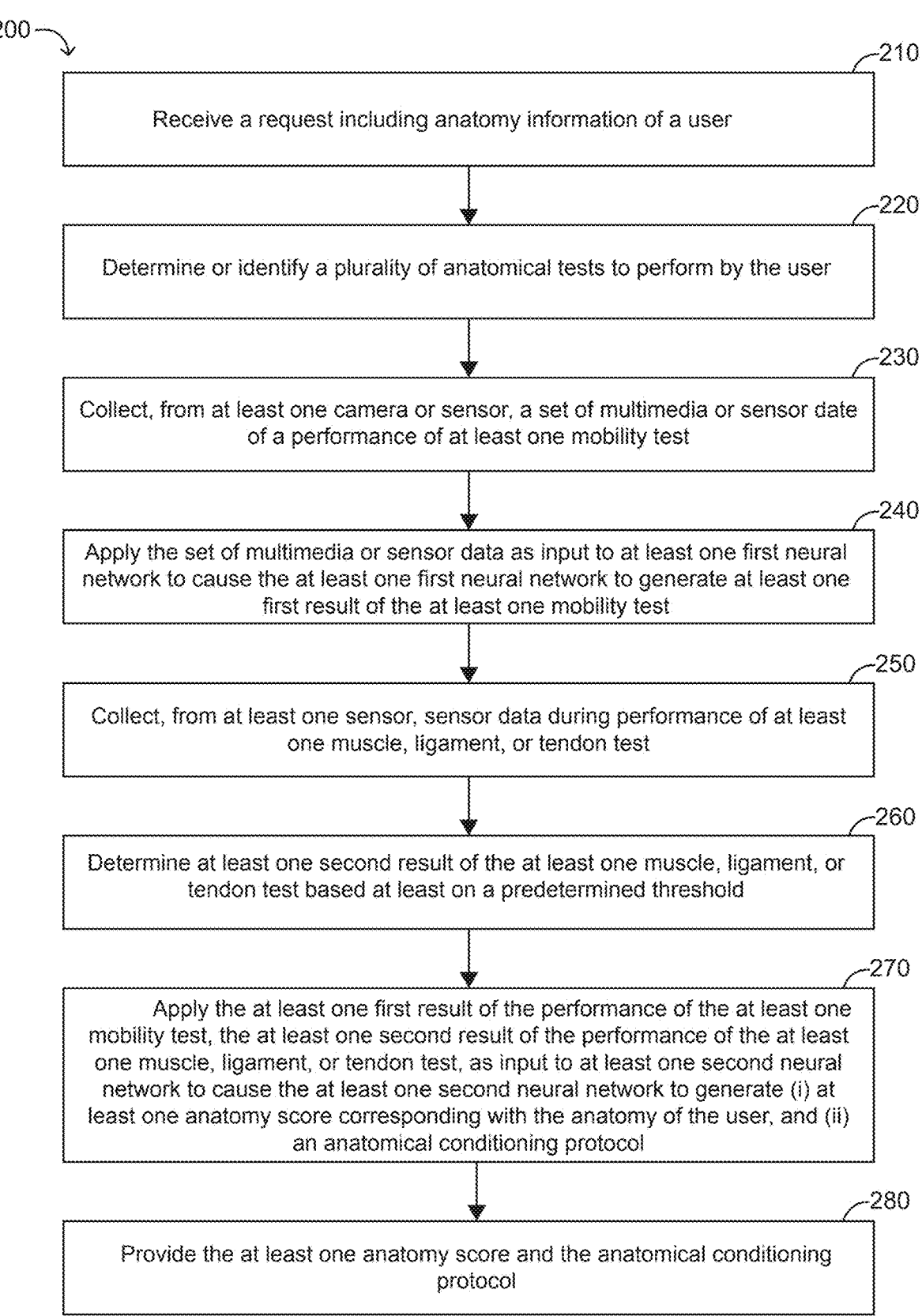

200

210
Receive a request including anatomy information of a user

220
Determine or identify a plurality of anatomical tests to perform by the user 230
Collect, from at least one camera or sensor, a set of multimedia or sensor date of a performance of at least one mobility test 240
Apply the set of multimedia or sensor data as input to at least one first neural network to cause the at least one first neural network to generate at least one first result of the at least one mobility test 250
Collect, from at least one sensor, sensor data during performance of at least one muscle, ligament, or tendon test 260
Determine at least one second result of the at least one muscle, ligament, or tendon test based at least on a predetermined threshold 270
Apply the at least one first result of the performance of the at least one mobility test, the at least one second result of the performance of the at least one muscle, ligament, or tendon test, as input to at least one second neural network to cause the at least one second neural network to generate (i) at least one anatomy score corresponding with the anatomy of the user, and (ii) an anatomical conditioning protocol 280
Provide the at least one anatomy score and the anatomical conditioning protocol

FIG. 2

Patient Output

Name: | John Doe
Data: | September 3, 2024
Age: | 40
Height: | 5'9"
Weight: | 215
BMI: | 31.7

Test Results (Compared to Peers in the Same Age Group)

Mobility Tests: Average

Muscle Tests: Below Average

Broad Jump: Above Average

Overall Bio-mechanical Optimum Output Score:

67

Legend
Good
Mild
At Risk

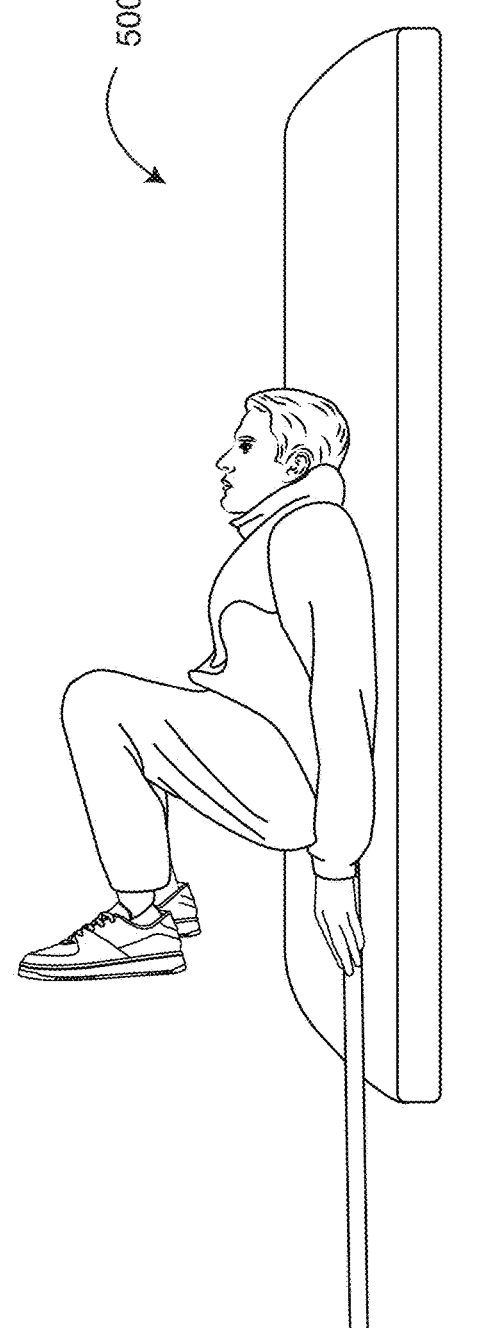
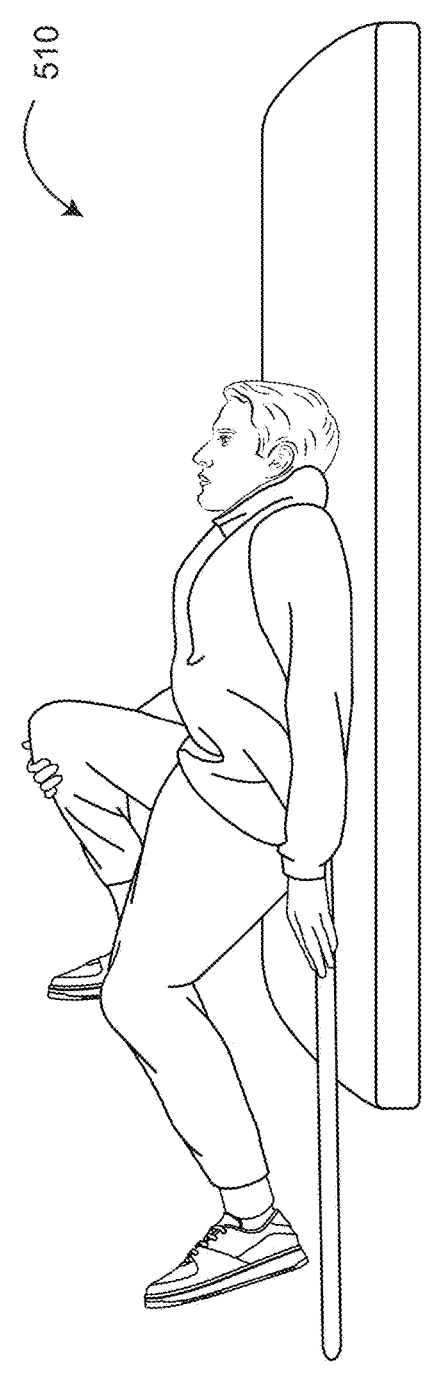
FIG. 5A

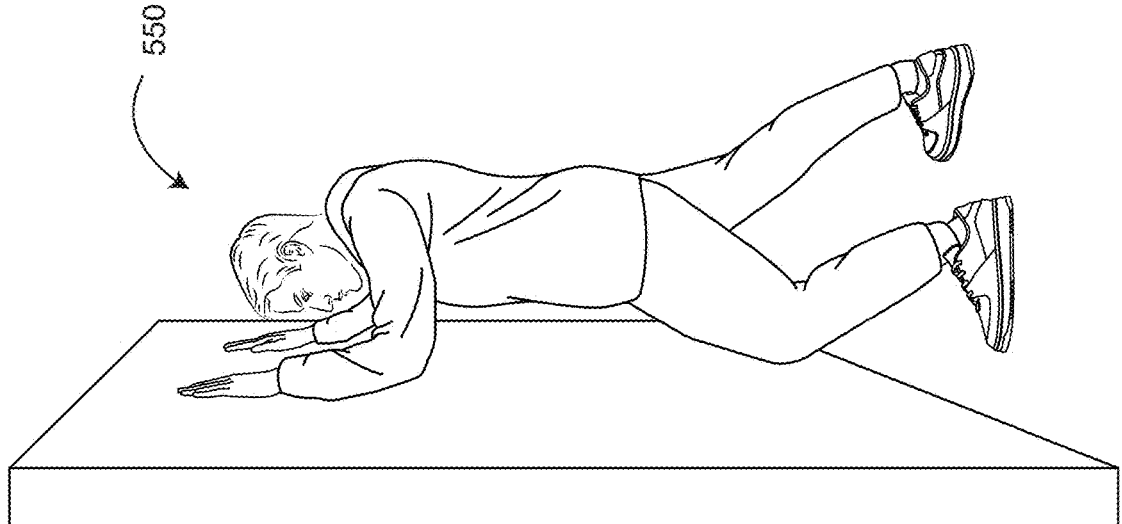
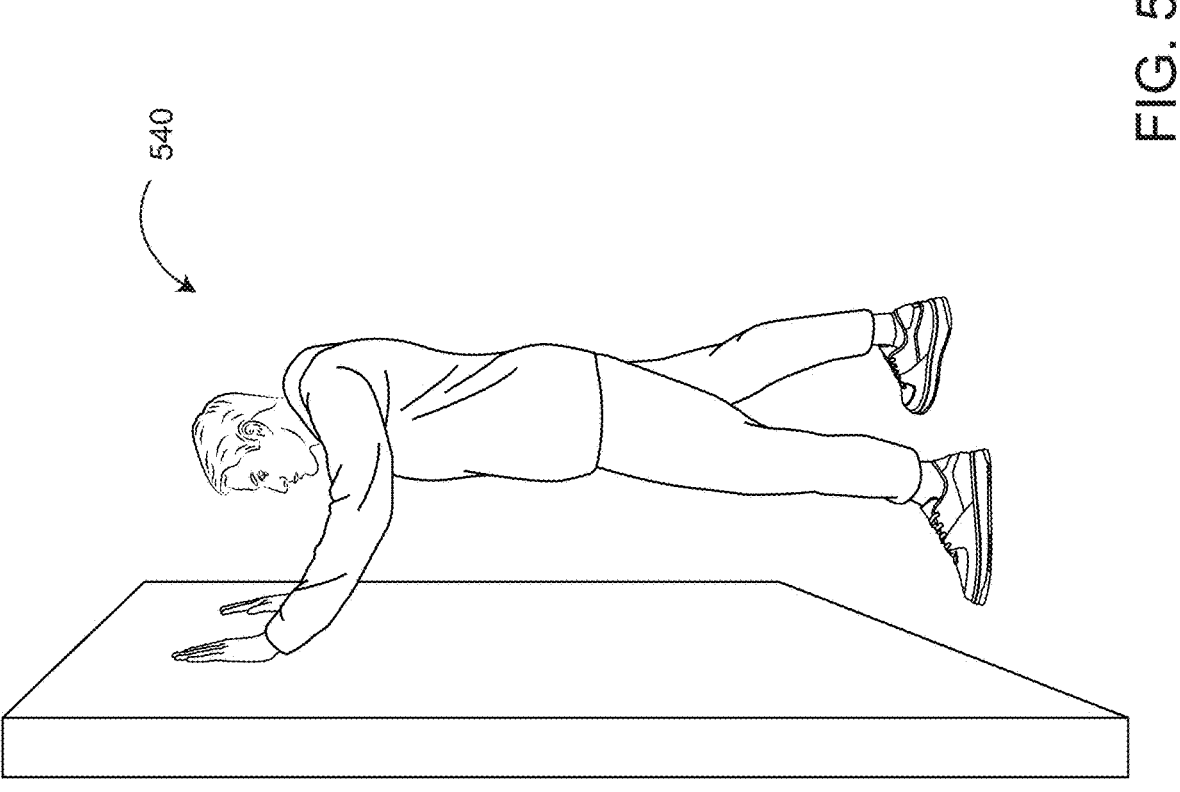
FIG. 5C

SYSTEMS AND METHODS FOR ANATOMICAL AND INJURY MODELING

BACKGROUND

Traditional methods for assessing and addressing the physical condition of a body often rely on manual evaluations conducted by professionals, such as healthcare practitioners or fitness experts. These evaluations typically involve various physical tests, which are subject to human interpretation and potential inconsistency. Moreover, traditional methods cannot provide real-time adjustments or personalized plans based on the dynamic physiological data collected from the individual during these assessments. As a result, individuals can receive generalized recommendations or protocols that do not account for their unique physical characteristics, objectives, or needs.

SUMMARY

Implementations of the present disclosure relate to systems and methods for providing personalized physical assessments and adaptive conditioning protocols using sensors, cameras, graphical interfaces, and/or machine learning models. The disclosed systems and methods can utilize one or more neural networks to analyze multimedia data and sensor data collected during various physiological tests, which can assess different aspects of the physical state of an individual. In some implementations, the systems and methods can generate a physical assessment, represented as one or more anatomy scores and/or subscores that corresponds to the current physical condition of the individual. Furthermore, the systems and methods can generate a personalized conditioning protocol that includes exercises or activities tailored to the specific physical objectives of the individual.

Some implementations relate to a method. The method can include receiving, by one or more processing circuits, a request including anatomy information of a user and an objective of an anatomy of the user. The method can include determining or identifying, by the one or more processing circuits, a plurality of anatomical tests to perform by the user. The method can include collecting, by the one or more processing circuits from at least one camera or sensor, a set of multimedia or sensor data of a performance of at least one mobility test of the plurality of anatomical tests performed by the user. The method can include applying, by the one or more processing circuits, the set of multimedia or sensor data as input to at least one first neural network to cause the at least one first neural network to generate at least one first result of the at least one mobility test. The method can include collecting, by the one or more processing circuits from at least one sensor, sensor data during performance of at least one muscle, ligament, or tendon test of the plurality of anatomical tests performed by the user. The method can include determining, by the one or more processing circuits, at least one second result of the at least one muscle, ligament, or tendon test based at least on a predetermined threshold. The method can include applying, by the one or more processing circuits, the at least one first result of the performance of the at least one mobility test, the at least one second result of the performance of the at least one muscle, ligament, or tendon test, the anatomy information, and objective of the anatomy of the user as input to at least one second neural network to cause the at least one second neural network to generate (i) at least one anatomy score corresponding with the anatomy of the user, and (ii) an anatomical conditioning protocol including at least a plurality of anatomy exercises. The method can include providing, by the one or more processing circuits, the at least one anatomy score and the anatomical conditioning protocol.

In some implementations, the method can further include monitoring, by the one or more processing circuits, a progress of the anatomical conditioning protocol based on (i) receiving an indication of a performance by the user, and (ii) determining the progress based at least on comparing the indication of the performance with at least one of the plurality of anatomy exercises. In some implementations, the at least one anatomy score includes a plurality of anatomy subscores corresponding with a plurality of regions or portions of the anatomy of the user. In some implementations, the method can further include generating, by the one or more processing circuits, a graphical user interface (GUI) including an anatomical outline of the anatomy of the user, wherein the anatomical outline includes at least one indicator corresponding at least one of the plurality of regions or portions of the anatomy of the user, and wherein the at least one indicator represents a prediction of a future condition of at least one of the plurality of regions or portions of the anatomy of the user based at least on a corresponding anatomy subscore of the plurality of anatomy subscores. In some implementations, the method can further include providing, by the one or more processing circuits, the GUI including the at least one indicator, the at least one anatomy score, and the plurality of anatomy subscores, each of the plurality of anatomy subscores corresponding to at least one of the plurality of regions or portions of the anatomy of the user, wherein the at least one indicator categorizes each of the plurality of regions or portions into a first category representing a favorable condition, a second category representing a mild condition, and a third category representing an at-risk condition based at least on the corresponding anatomy subscore.

In some implementations, the anatomical conditioning protocol includes an exercise or recovery routine corresponding with a frequency and duration of at least one of the plurality of anatomy exercises, wherein the method further includes receiving, by the one or more processing circuits, performance data of the user and updating, by the one or more processing circuits, the exercise or recovery routine based at least on the performance data. In some implementations, the method can further include generating, by the one or more processing circuits, a prompt based on at least the anatomy information, the at least one first result of the at least one mobility test, and the at least one second result of the at least one muscle, ligament, or tendon test, wherein generating the prompt includes identifying one or more anatomical conditions of the user and the objective of the anatomy of the user. In some implementations, the method can further include monitoring, by the one or more processing circuits, a progress of the user performing the anatomical conditioning protocol based at least on one of receiving application data of a user device of the user or a third-party, receiving, via an interface, an input from the user or the third-party, or receiving an input from a sensor device positioned to monitor the user or coupled to the user.

In some implementations, the method can further include identifying, by the one or more processing circuits, a context based at least on the objective of the anatomy of the user, wherein the context corresponds to one or more regions, muscles, ligaments, or tendons of the anatomy of the user, and wherein the anatomical conditioning protocol including the plurality of anatomy exercises include a targeted rehabilitation or targeted development of the one or more regions, muscles, ligaments, or tendons of the anatomy of the user. In some implementations, the at least one first neural network is applied to the set of multimedia or sensor data to analyze the at least one mobility test based at least on comparing a range of motion in the set of multimedia or sensor data to one or more predefined mobility thresholds and determining the at least one first result of the at least one mobility test based on the user meeting or exceeding the one or more predefined mobility thresholds.

In some implementations, determining the at least one second result of the at least one muscle, ligament, or tendon test includes aggregating and averaging a plurality of muscle, ligament, or tendon tests of at least one muscle, ligament, or tendon of the user, and wherein the sensor data includes one or more force measurements from the at least one sensor positioned to monitor at least one muscle, ligament, or tendon corresponding with the at least one muscle, ligament, or tendon test. In some implementations, the method can further include responsive to a predetermined schedule, generating, by the one or more processing circuits, at least one updated anatomy score based at least on applying one or more updated results of performance of the at least one mobility test or the at least one muscle, ligament, or tendon test, the anatomy information, and the objective or an updated objective of the anatomy of the user as input to the at least one second neural network to cause the at least one second neural network to generate the at least one updated anatomy score corresponding with the anatomy of the user.

Some implementations relate to a system including one or more processing circuits configured to receive a request including anatomy information of a user and an objective of an anatomy of the user. The one or more processing circuits can be further configured to determine or identify a plurality of anatomical tests to perform by the user. The one or more processing circuits can be further configured to collect, from at least one camera or sensor, a set of multimedia or sensor data of a performance of at least one mobility test of the plurality of anatomical tests performed by the user. The one or more processing circuits can be further configured to apply the set of multimedia or sensor data as input to at least one first neural network to cause the at least one first neural network to generate at least one first result of the at least one mobility test. The one or more processing circuits can be further configured to collect, from at least one sensor, sensor data during performance of at least one muscle, ligament, or tendon test of the plurality of anatomical tests performed by the user. The one or more processing circuits can be further configured to determine at least one second result of the at least one muscle, ligament, or tendon test based at least on a predetermined threshold. The one or more processing circuits can be further configured to apply the at least one first result of the performance of the at least one mobility test, the at least one second result of the performance of the at least one muscle, ligament, or tendon test, the anatomy information, and objective of the anatomy of the user as input to at least one second neural network to cause the at least one second neural network to generate (i) at least one anatomy score corresponding with the anatomy of the user, and (ii) an anatomical conditioning protocol including at least a plurality of anatomy exercises. The one or more processing circuits can be further configured to provide the at least one anatomy score and the anatomical conditioning protocol.

In some implementations, one or more processing circuits are further configured to monitor a progress of the anatomical conditioning protocol based on (i) receiving an indication of a performance by the user, and (ii) determining the progress based at least on comparing the indication of the performance with at least one of the plurality of anatomy exercises. In some implementations, the at least one anatomy score includes a plurality of anatomy subscores corresponding with a plurality of regions or portions of the anatomy of the user.

In some implementations, the one or more processing circuits are further configured to generate a graphical user interface (GUI) including an anatomical outline of the anatomy of the user, wherein the anatomical outline includes at least one indicator corresponding at least one of the plurality of regions or portions of the anatomy of the user, and wherein the at least one indicator represents a prediction of a future condition of at least one of the plurality of regions or portions of the anatomy of the user based at least on a corresponding anatomy subscore of the plurality of anatomy subscores. In some implementations, the one or more processing circuits are further configured to provide the GUI including the at least one indicator, the at least one anatomy score, and the plurality of anatomy subscores, each of the plurality of anatomy subscores corresponding to at least one of the plurality of regions or portions of the anatomy of the user, wherein the at least one indicator categorizes each of the plurality of regions or portions into a first category representing a favorable condition, a second category representing a mild condition, and a third category representing an at-risk condition based at least on the corresponding anatomy subscore.

In some implementations, the anatomical conditioning protocol includes an exercise or recovery routine corresponding with a frequency and duration of at least one of the plurality of anatomy exercises. In some implementations, the one or more processing circuits are further configured to receive performance data of the user and update the exercise or recovery routine based at least on the performance data. In some implementations, one or more processing circuits are further configured to generating, by the one or more processing circuits, a prompt based on at least the anatomy information, the at least one first result of the at least one mobility test, and the at least one second result of the at least one muscle, ligament, or tendon test, wherein generating the prompt includes identifying one or more anatomical conditions of the user and the objective of the anatomy of the user.

In some implementations, the one or more processing circuits are further configured to monitor a progress of the user performing the anatomical conditioning protocol based at least on one of receiving application data of a user device of the user or a third-party, receiving, via an interface, an input from the user or the third-party, or receiving an input from a sensor device positioned to monitor the user or coupled to the user. In some implementations, one or more processing circuits are further configured to identify a context based at least on the objective of the anatomy of the user, wherein the context corresponds to one or more regions, muscles, ligaments, or tendons of the anatomy of the user, and wherein the anatomical conditioning protocol including the plurality of anatomy exercises include a targeted rehabilitation or targeted development of the one or more regions, muscles, ligaments, or tendons of the anatomy of the user.

Some implementations relate to a non-transitory computer readable medium including one or more instructions stored thereon, and when the one or more instructions are executed by at least one processor causes the at least one processor to execute operations of receiving a request including anatomy information of a user and an objective of an anatomy of the user. The non-transitory computer readable medium including the one or more instructions stored thereon, and when the one or more instructions are executed by the at least one processor causes the at least one processor to execute operations of determining or identifying a plurality of anatomical tests to perform by the user. The non-transitory computer readable medium including the one or more instructions stored thereon, and when the one or more instructions are executed by the at least one processor causes the at least one processor to execute operations of collecting, from at least one camera or sensor, a set of multimedia or sensor data of a performance of at least one mobility test of the plurality of anatomical tests performed by the user. The non-transitory computer readable medium including the one or more instructions stored thereon, and when the one or more instructions are executed by the at least one processor causes the at least one processor to execute operations of applying the set of multimedia or sensor data as input to at least one first neural network to cause the at least one first neural network to generate at least one first result of the at least one mobility test. The non-transitory computer readable medium including the one or more instructions stored thereon, and when the one or more instructions are executed by the at least one processor causes the at least one processor to execute operations of collecting, from at least one sensor, sensor data during performance of at least one muscle, ligament, or tendon test of the plurality of anatomical tests performed by the user. The non-transitory computer readable medium including the one or more instructions stored thereon, and when the one or more instructions are executed by the at least one processor causes the at least one processor to execute operations of determining at least one second result of the at least one muscle, ligament, or tendon test based at least on a predetermined threshold. The non-transitory computer readable medium including the one or more instructions stored thereon, and when the one or more instructions are executed by the at least one processor causes the at least one processor to execute operations of applying the at least one first result of the performance of the at least one mobility test, the at least one second result of the performance of the at least one muscle, ligament, or tendon test, the anatomy information, and objective of the anatomy of the user as input to at least one second neural network to cause the at least one second neural network to generate (i) at least one anatomy score corresponding with the anatomy of the user, and (ii) an anatomical conditioning protocol including at least a plurality of anatomy exercises. The non-transitory computer readable medium including the one or more instructions stored thereon, and when the one or more instructions are executed by the at least one processor causes the at least one processor to execute operations of providing the at least one anatomy score and the anatomical conditioning protocol.

BRIEF DESCRIPTION OF THE DRAWINGS

The present systems and methods for systems and methods for anatomical and injury modeling are described in detail below with reference to the attached drawing figures, wherein:

FIG. 2 depicts a method for anatomical and injury modeling, in accordance with some implementations of the present disclosure;

FIGS. 5A-5C depict example tests, in accordance with some implementations of the present disclosure;

Figure 1:
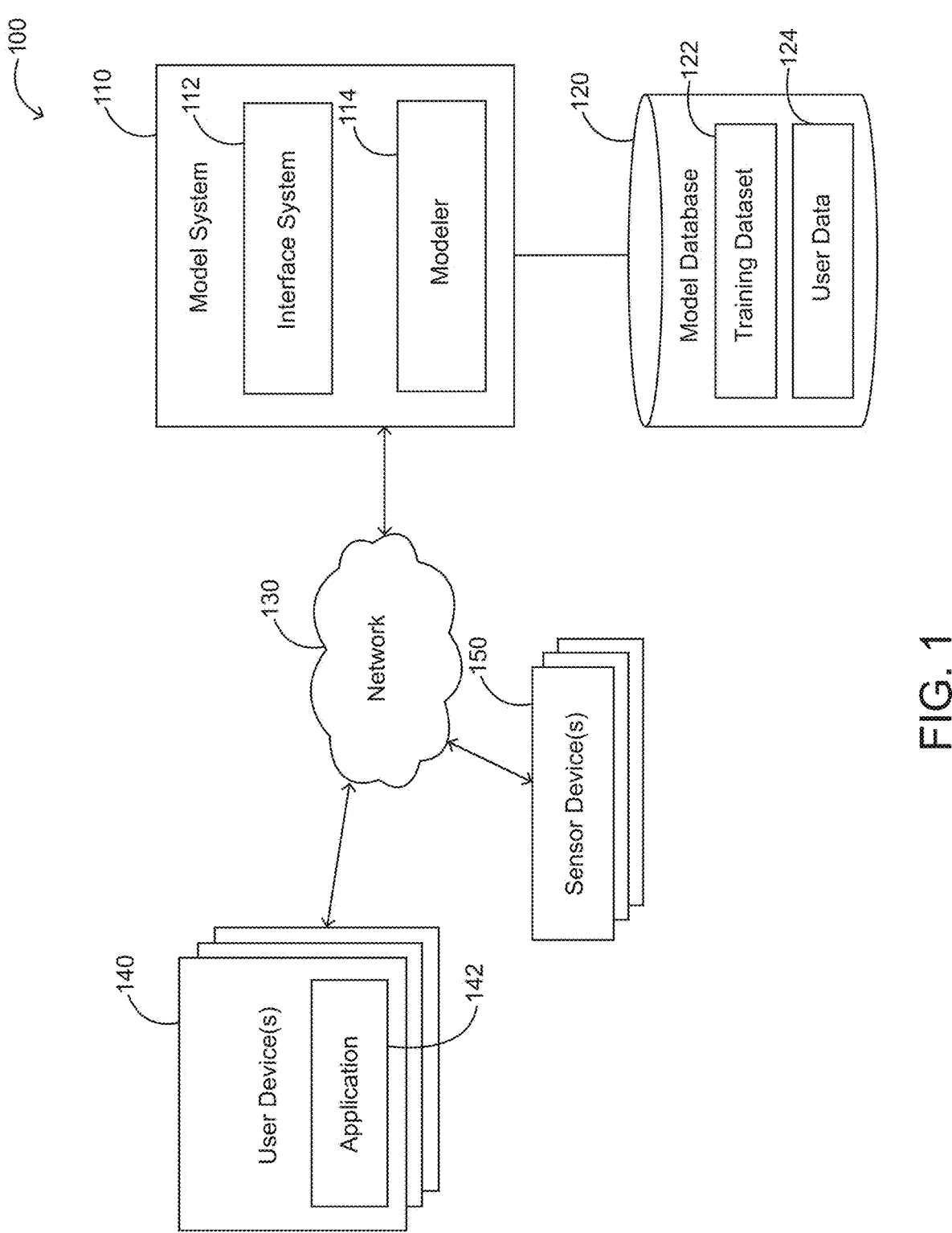
FIG. 1 is a block diagram of an example of a system, in accordance with some implementations of the present disclosure.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

This disclosure relates to systems and methods for modeling and managing anatomical conditions and generating personalized conditioning protocols designed to prevent potential injuries before they occur. By using multimedia data, sensor data, and/or other user data, the systems and methods can identify areas within the anatomy of the user that can be susceptible to injury, such as ligament tears, muscle strains, or joint instability. That is, the systems and methods disclosed herein can be implemented to analyze real-time (or near real-time) data gathered during various anatomical tests, such as tests related to mobility, muscle performance, ligament strength, or tendon health, among other possible anatomical assessments. These tests can be performed in a wide range of environments, such as fitness centers, rehabilitation facilities, or even in-home settings, using one or more sensors (e.g., of a sensor device, instrument(s), or mobile device), cameras (e.g., of an instrument, mobile device, and/or other camera device), other muscle testing and range of motion devices (e.g., 2-in-1 goniometers, dynamometers, inclinometers, accelerometers, electromyography (EMG) sensors, strain gauges) or other multimedia devices to capture data related to the anatomy and movement of the user. The systems and methods can process and model the data using machine learning models, including vision-based models for analyzing test performance, and provide actionable feedback through an anatomy score. The anatomy score and associated subscores can identify specific anatomical vulnerabilities and areas for improvement. The systems and methods can also generate a personalized conditioning protocol, including for example, tailored exercises and routines, to proactively address these identified risks and improve the overall physical condition of the user.

Traditional systems for anatomical assessment typically focus on treating or responding to injuries after they occur, relying on generalized evaluations or manual testing to provide conditioning recommendations. However, such systems lack the capability to foresee potential anatomical weaknesses before they lead to injury. Additionally, these systems face technical challenges in modeling and analyzing multi-dimensional data from the body of the user, such as data from mobility and strength tests. Traditional systems often fail to generate accurate, isolated metrics for specific body regions, leading to generalized or incomplete assessments. Moreover, existing approaches fail to provide personalized conditioning protocols based on real-time data or adaptive feedback from ongoing performance. As a result, the lack of precise modeling and data analysis leads to insufficient detection of potential injuries and inadequate conditioning strategies, leaving the individual at risk for conditions such as ligament tears, joint damage, or muscle strains. That is, traditional treatment plans are often standardized rather than tailored and/or customized to the unique characteristics of the individual, resulting in protocols that can fail to address specific anatomical vulnerabilities or personal goals. Consequently, these generalized approaches overlook the nuanced requirements of each individual, which can hinder injury prevention and limit the effectiveness of rehabilitation efforts.

In contrast, systems and methods according to the present disclosure provide a technical solution to injury prevention by identifying potential weaknesses or areas of stress within the anatomy of the user before they manifest into injuries. The systems and methods can implement the technical solution by using one or more vision-based models, instruments, and/or capture devices to perform anatomical tests, such as mobility or strength assessments, by analyzing real-time multimedia data, such as video, audio, and/or images of the user performing specific movements. The vision model can model the movements of the user, identifying irregularities or patterns that suggest potential vulnerabilities in specific regions of the body. Additionally, sensor data from devices such as force sensors or motion detectors can be collected during various tests, providing quantitative data on muscle strength, ligament tension, or joint stability.

The systems and methods can apply the results of these tests to one or more machine learning models to generate an anatomy score. The anatomy score can represent an overall assessment of the current anatomical condition of the user, while associated subscores correspond to specific regions or portions of the body. For example, if the model output detects excessive strain in the knee ligaments of the user during testing, the subscore for that region can indicate a potential risk for an anterior cruciate ligament (ACL) tear. Based on the generated anatomy scores and subscores, the systems and methods can identify points or areas of improvement that can prevent future injuries. In some implementations, model can generate a personalized anatomical conditioning protocol, including tailored exercises to address these specific areas of concern.

For example, if the modeling and outputs identify or determine an ACL of a user is at risk due to instability or weakness in the surrounding muscles, the conditioning protocol can include targeted strengthening exercises for the quadriceps, hamstrings, or other supporting structures. The exercise can be outputted by the model based on the model applying the input (e.g., at least one first result of the performance of the at least one mobility test, at least one second result of the performance of the at least one muscle, ligament, or tendon test, anatomy information, and/or objective of the anatomy of the user) and generating an anatomy score and subscores corresponding to the affected regions of the body. That is, the personalized conditioning protocol can be used to reduce the likelihood of injury by improving the identified vulnerable areas before an injury can occur. The conditioning protocol can be continually (or periodically) updated and adjusted based on new data collected from subsequent tests, allowing the systems and methods to dynamically adapt to the progress and changing anatomical condition of the user. Thus, the technical solution of using multi-layered neural networks and data-driven models to process sensor and multimedia input, generate localized anatomical subscores, and dynamically update personalized conditioning protocols solves the technical problem of inefficient and imprecise identification of anatomical vulnerabilities by isolating potential areas of failure with predictive accuracy, allowing for proactive conditioning adjustments.

The systems and methods can also provide a graphical user interface (GUI) where users can view their anatomy scores and subscores, along with visual indicators that correspond to different regions of the body. For example, the indicators can highlight areas of concern, providing the user with a clear understanding of which parts of their body can require attention. The assessment of the anatomy of the user using modeling and data analysis to provide customized conditioning protocols based on the modelling allows for improved injury prevention strategies, allowing the user to improve physical conditions in a safe and personalized framework. Therefore, the technical solution of integrating a vision-based model to analyze physical movement and anatomical data with visual representation in GUIs of isolated subscores and predictive indicators, solves the technical problem of generalized or incomplete anatomical assessments by providing a modeling technique to injury prediction and personalized anatomical conditioning that can update based on real-time (or near real-time) input.

With reference to FIG. 1, FIG. 1 is an example block diagram of a system 100, in accordance with some implementations of the present disclosure. It should be understood that this and other implementations described herein are set forth only as examples. Other implementations and elements (e.g., machines, interfaces, functions, orders, groupings of functions, etc.) can be used in addition to or instead of those shown, and some elements can be omitted altogether. Further, many of the elements described herein are functional entities that can be implemented as discrete or distributed components or in conjunction with other components, and in any combination and location. Various functions described herein as being performed by entities can be carried out by hardware, firmware, and/or software. For example, various functions can be carried out by a processor executing instructions stored in memory. In some implementations, the systems, methods, and processes described herein can be executed using similar components, features, and/or functionality to those of example computing system 400 of FIG. 4.

The system 100 can also include a model database 120 having a training dataset 122 and user data 124 (e.g., including customer data, client data, third-party data (e.g., data from partnered fitness trackers, health applications, sports organizations, medical providers), and/or any data contributing to improve anatomical assessments). The system 100 can also include a model system, shown as model system 110, having a non-transitory computer readable medium, processing circuit, processor, memory, interface system 112, and/or modeler 114. The system 100 can also include a user computing system, shown as user device(s) 140, having a processing circuit, processor, memory, and application 142. The system 100 can also include sensor device(s), shown as sensor device(s) 150, having a processing circuit, processor, and/or memory. The components of the system 100 can be connected, or in wired or wireless communication, via a network 130. It should be understood that the number and type of components shown is merely illustrative and, in various implementations, implementations of the system 100 can have additional, fewer, and/or different components than those illustrated in FIG. 1 including, those mentioned elsewhere herein.

The components of the system 100 can be connected, or in communication, via a network 130. Network 130 can include computer networks such as the Internet, local, wide, metro or other area networks, intranets, satellite networks, other computer networks such as voice or data mobile phone communication networks, combinations thereof, or any other type of electronic communications network. Network 130 can include or constitute a display network. In some implementations, network 130 facilitates secure communication between components of system 100. As a non-limiting example, network 130 can implement transport layer security (TLS), secure sockets layer (SSL), hypertext transfer protocol secure (HTTPS), and/or any other secure communication protocol. It should be noted that the number and type of components shown are merely illustrative, and in various implementations, implementations of the system 100 can have additional, fewer, and/or different components than those illustrated in FIG. 1. In some implementations, the network 130 can facilitate communication between various nodes, such as the model system 110, the user devices 140, the sensor device(s) 150, and the model database 120. In some implementations, data flows through the network 130 from a source node to a destination node as a flow of data packets, e.g., in the form of data packets in accordance with the Open Systems Interconnection (OSI) layers. A flow of packets can use, for example, an OSI layer-4 transport protocol such as the User Datagram Protocol (UDP), the Transmission Control Protocol (TCP), or the Stream Control Transmission Protocol (SCTP), transmitted via the network 130 layered over an OSI layer-3 network protocol such as Internet Protocol (IP), e.g., IPv4 or IPv6.

In some implementations, the network 130 can be composed of various network devices (nodes) that are communicatively linked to form one or more data communication paths between participating devices. Each networked device can include at least one network interface for receiving and/or transmitting data, typically as one or more data packets. An illustrative network 130 is the Internet; however, other networks can be used. The network 130 can be an autonomous system (AS), i.e., a network that can be operated under a consistent unified routing policy (or at least appears to be from outside the AS network) and generally managed by a single administrative entity (e.g., a system operator, administrator, or administrative group).

Generally, the model system 110, user devices 140, sensor devices 150, and model database 120 can include one or more logic devices, which can be one or more computing devices equipped with one or more processing circuits that run instructions stored in a memory device to perform various operations. The processing circuit can be made up of various components such as a microprocessor, an ASIC, or an FPGA, and the memory device can be any type of storage or transmission device capable of providing program instructions. The instructions can include code from various programming languages commonly used in the industry, such as high-level programming languages, web development languages, and system programming languages. The model system 110, user devices 140, and sensor devices 150 can also include one or more databases for storing data, such as model database 120, that receive and provide data to other systems and devices on the network 130.

In some implementations, each system or device in system 100 can include one or more processors, memories, network interfaces (sometimes referred to herein as a "network circuit") and user interfaces. The memory can store programming logic that, when executed by the processor controls the operation of the corresponding computing system or device. The memory can also store data in a database (e.g., model database 120). For example, a memory can store programming logic that, when executed by processor within processing circuit, causes model database 120 to update user information in user data 124. The network interfaces can allow the computing systems and devices to communicate wirelessly or otherwise. The various components of devices in system 100 can be implemented via hardware (e.g., circuitry), software (e.g., executable code), or any combination thereof. Devices, systems, and components in FIG. 1 can be added, deleted, integrated, separated, and/or rearranged in various implementations of the disclosure.

In some implementations, the model database 120 can be configured to store and organize data used in modeling by the model system 110. The data can include the training dataset 122 and the user data 124. The training dataset 122 can include training data used to develop and refine the AI models within the model system 110. For example, the training dataset 122 can include motion capture data, sensor readings from previous users, labeled biomechanical data (e.g., joint angles, force outputs), results from strength and flexibility tests, population-level performance baselines, and/or any other datasets relevant to training neural networks for anatomical assessments. The user data 124 can store information about users, profiles of the users, test results, historical performance metrics, anatomical scores, and/or any other data related to individual user assessments. For example, the user data 124 can include demographic information of the user (e.g., age, gender, weight), past injury reports, test results from mobility and strength assessments, anatomical conditioning protocols, exercise compliance data, and/or any data used to personalize the conditioning protocol for the user.

As will be discussed in greater detail below, the model system 110 can be configured to receive a request including anatomy information of a user and an objective of an anatomy of the user. The model system 110 can process this request through the interface system 112, where it captures both the anatomy information and objective of the user. That is, the model system 110 can receive data such as user-specific anatomy measurements (e.g., height, weight, medical history) and objectives (e.g., improvement of joint flexibility or rehabilitation). For example, the model system 110 can receive this request through a client intake form on a web interface of a user device 140, which is then transmitted through the network 130 and stored in the user data 124 in the model database 120. In some implementations, the anatomy information can include a breakdown of muscle strength, flexibility, or known injuries, and the objective can specify desired outcomes such as injury prevention or recovery.

As will be discussed in greater detail below, the model system 110 can be configured to receive a request including anatomy information of a user and an objective of an anatomy of the user. The model system 110 can process this request through the interface system 112, where it captures both the anatomy information and objective of the user. That is, the model system 110 can receive data such as user-specific anatomy measurements (e.g., height, weight, medical history, injury history, previous treatments, and/or biomechanic compensations of the body (e.g., improper squat alignment where knees can collapse inward, uneven weight distribution on feet during lunges, torso leaning excessively forward during squats, hip drop in a single-leg stance, or compensatory shoulder elevation during overhead movements)) and objectives (e.g., improvement of joint flexibility, rehabilitation, strength improvement, injury prevention). For example, the model system 110 can receive this request through a client intake form on a web interface of a user device 140, which is then transmitted through the network 130 and stored in the user data 124 in the model database 120. In some implementations, the anatomy information can include a breakdown of muscle strength, flexibility, or known injuries (e.g., torn ligaments, weakened muscles, previous surgeries), and the objective can specify desired outcomes such as injury prevention, recovery, or overall physical improvement. For example, the model system 110 can be used by athletes to prevent ligament injuries, indicating their prevention as an objective.

In some implementations, the model system 110 can be configured to determine or identify a plurality of anatomical tests to be performed by the user. The model system 110 can use the anatomy information and objective to select a series of tests from its predefined test database (e.g., stored in model database 120, categorized by injury type, joint flexibility, muscle strength). That is, the model system 110 can analyze the received data to determine which anatomical tests (e.g., mobility, flexibility, strength assessments, balance tests) are appropriate for the objective of the user. For example, the model system 110 can select mobility and strength tests for the lower body if the objective of the user is to improve leg stability (e.g., recovering from a knee injury, enhancing leg muscle strength). In some implementations, the model system 110 can generate new tests and/or update existing tests based on the condition of the user. For example, the model system 110 can update tests as the user progresses through rehabilitation by dynamically adjusting testing difficulty. In some implementations, the model system 110 can cross-reference the anatomy information of the user with past performance data in the model database 120 to select tests that match the physical profile of the user (e.g., age, gender, physical limitations). For example, a user with a focus on preventing shoulder injuries can have shoulder-specific mobility tests selected and modified to target potential areas of weakness over time. Additionally, the model system 110 can prioritize specific tests based on the objective of the user, such as selecting muscle tests for users focused on injury prevention (e.g., preventing rotator cuff tears, avoiding joint instability). For example, a user with a focus on preventing shoulder injuries can have a set of shoulder-specific mobility tests selected by the model system 110 to evaluate joint flexibility and identify early signs of instability or muscle imbalance in the rotator cuff region.

In some implementations, the model system 110 can be configured to collect, from at least one camera or sensor, a set of multimedia or sensor data of a performance of at least one mobility test of the plurality of anatomical tests performed by the user. The model system 110 can retrieve this data in real-time as the user performs the anatomical tests. That is, the model system 110 can gather video footage, motion tracking data, accelerometer readings, gyroscopic data, joint angle measurements, and/or any other biomechanical data from a user device 140 or a sensor device 150 during the test. For example, the interface system 112 can collect data from a camera-enabled user device 140 that captures the range of motion of the user during a knee flexion test. In some implementations, sensor devices 150, such as pressure sensors, wearable motion trackers, or other force measurement devices, can be used to capture biomechanical data such as joint angles or muscle activation patterns. Additionally, the collected data can be stored in the user data 124 (e.g., associated with a profile or rehabilitation plan of the user) in the model database 120 for further processing. For example, the multimedia data collected during a mobility test can be processed to calculate joint flexibility and movement efficiency (e.g., range of motion, joint stability, muscle coordination). In some implementations, a profile can be created (e.g., stored in user data 124) for a user such that subsequent test results can be compared to initial performance, generating progress tracking data (e.g., improvement in flexibility, reduction in instability). That is, the model system 110 can continuously update the profile of the user based on the results of mobility tests. For example, progress can be tracked by comparing the initial range of motion against subsequent tests to evaluate improvements.

In some implementations, the model system 110 can be configured to apply (e.g., by the modeler 114) the set of multimedia or sensor data as input to at least one first neural network to cause the at least one first neural network to generate at least one first result of the at least one mobility test. The model system 110 can process the multimedia or sensor data through modeler 114, which can apply the data to the neural network for analysis. That is, the neural network can receive input data such as video footage or sensor readings and generate a result based on predefined mobility thresholds. For example, the model system 110 can process video data and/or other captured data (e.g., images, audio) from a knee flexion test, and the neural network can output a pass/fail result based on whether the range of motion exceeding the threshold for normal mobility. In some implementations, the first neural network can generate additional results, such as joint stability or range of motion percentages. Additionally, the neural network can use previously trained models stored in the training dataset 122 to refine its output. For example, the neural network can predict the overall mobility score of the user based on the captured data. In some implementations, the neural network can detect correlations between distinct anatomical areas (e.g., identifying gluteal weakness associated with a knee injury, shoulder instability correlated with core weakness, etc.). This allows the neural network to identify biomechanical compensations or interdependencies that may not be readily apparent in standard assessments, facilitating conditioning protocols that account for both direct and compensatory weaknesses. Furthermore, by incorporating and analyzing new data over time, the neural network can identify biomechanical patterns and injury predispositions, providing outputs that can refine or improve traditional clinical understanding and guide targeted intervention strategies.

The system 100 can include at least one modeler 114. The modeler 114 can include any one or more artificial intelligence models (e.g., vision models, machine learning models, supervised models, neural network models, deep neural network models), rules, heuristics, algorithms, functions, or various combinations thereof to perform operations including mobility analysis, joint angle detection, and movement tracking, such as evaluating range of motion and detecting abnormal movement patterns. That is, a vision model can be a neural network trained to identify anatomical landmarks (e.g., joints, muscles, ligaments) and assess biomechanical movement (e.g., flexion, extension, rotation). In some implementations, the modeler 114 can output movement quality metrics (e.g., range of motion, joint stability, movement efficiency, and/or any performance metric). For example, the vision model can output a result indicating whether the knee flexion exceeds a predefined threshold for normal mobility. In another example, the vision model can output data related to shoulder joint stability during an overhead reach. In some implementations, the results from the vision model can be provided as input to another model of the modeler 114 to generate at least one anatomy score corresponding with the anatomy of the user and/or an anatomical conditioning protocol including at least a plurality of anatomy exercises (e.g., calf raises, jump squats land on both feet, pull ups hold knees to chest, seated soleus raises, jump squats to land on one foot, single leg bridge with chest press, tib ant band, broad jump forward and land on one foot, push-up with renegade row, walking calf iso holds, lateral move and hold on one leg, high plank holds with contralateral raises, deadlift to calf raise among other exercises).

In some implementations, the modeler 114 can maintain, execute, train, and/or update one or more machine-learning models during application of the set of multimedia or sensor data as input. In some implementations, the machine-learning model(s) can include any type of deep learning machine-learning models capable of processing visual and sensor data (e.g., convolutional neural networks (CNNs), transformer-based models) to identify joint mechanics, motion ranges, and stability. For example, the machine-learning model(s) can be trained and/or updated to analyze motion capture data and detect patterns associated with muscle fatigue or ligament weakness, among other conditions. The machine-learning model(s) can be or include a transformer-based model (e.g., a generative pre-trained transformer (GPT) model) for biomechanical assessment. The machine-learning model(s) can be or include a CNN model, in some implementations. The modeler 114 can execute the machine-learning model to generate outputs such as mobility scores and/or mobility assessment reports. The modeler 114 can receive data to provide as input to the machine-learning model(s), which can include a set of multimedia or sensor data (e.g., from user device 140 and/or sensor devices 150).

The modeler 114 can include at least one neural network (e.g., vision model). The vision model can include an input layer, an output layer, and/or one or more intermediate layers, such as hidden layers, which can each have respective nodes. That is, the vision model can process data from sensors (e.g., video, accelerometers) through multiple layers to generate a mobility result. For example, the input layer can receive video footage of the user performing a knee flexion, and the vision model can identify anatomical points (e.g., knee, ankle, hip) to calculate the range of motion. In another example, the output layer can generate a pass/fail result based on whether the measured range of motion exceeds predefined thresholds. In yet another example, the intermediate layers can analyze the smoothness of the movement to assess joint stability. In some implementations, the training dataset 122 can be used to train the vision model with labeled motion capture data from a range of users (e.g., athletes, recovering patients). That is, the training dataset 122 can include joint angle data from mobility tests (e.g., ankle tests, hamstring tests, hip tests, IT band tests, among other tests), facilitating the training (e.g., by the vision model) to predict results based on these inputs. For example, the training dataset 122 can include measurements for knee flexion angles across different user profiles.

In some implementations, the modeler 114 can configure (e.g., train, update, fine-tune, apply transfer learning to) the vision model by modifying or updating one or more parameters, such as weights and/or biases, of various nodes of the vision model responsive to evaluating estimated outputs of the vision model (e.g., generated in response to receiving training examples in training dataset 122). The modeler 114 can be or include various neural network models, including models that can operate on or generate data including but not limited to joint angles, motion trajectories, muscle activation data, and/or various combinations thereof. For example, the modeler 114 can fine-tune the vision model by adjusting the weights associated with specific joint detection points based on test results from the performance data of the user. In some implementations, the fine-tuning can be applied to improve the accuracy of detecting small joint movements (e.g., ankle rotation, wrist extension).

In some implementations, the modeler 114 can be configured (e.g., trained, updated, fine-tuned, has transfer learning performed, etc.) based at least on the training data of the at least one training dataset 122. For example, a set of multimedia or sensor data and/or ground truth results of joint flexibility or muscle strength of the training data can be applied (e.g., by the modeler 114, or in a pre-training process performed by the modeler 114 or another system) as input to the modeler 114 to cause the modeler 114 to generate an estimated result (e.g., an output). The estimated result can be evaluated and/or compared with expected outcomes (or predefined mobility thresholds) of the training dataset 122 that correspond with the one or more example sets of multimedia or sensor data. The results can include visual data (e.g., video, motion tracking) and/or measurements of one or more body metrics (e.g., joint angles, muscle force, range of motion), and the vision model of the modeler 114 can be updated based at least on the comparison results and/or discrepancies found during evaluation. For example, based at least on an output of the vision model for a knee flexion test, one or more parameters (e.g., weights and/or biases) of the vision model of the modeler 114 can be updated.

In some implementations, the model system 110 can be configured to collect, from at least one sensor, sensor data during performance of at least one muscle, ligament, or tendon test of the plurality of anatomical tests performed by the user. The model system 110 can use sensor devices 150 to monitor the performance of muscle, ligament, or tendon tests. That is, the sensor devices 150 can capture data such as force output, muscle contraction, ligament flexibility, tendon elasticity, and/or any joint angle measurements during the tests. For example, the model system 110 can collect data from a strain gauge sensor that measures the force exerted by a user during a resistance test (e.g., during a leg press, isometric hold, or flexion test). In some implementations, wearable sensors (e.g., smartwatches, pressure sensors, electromyography (EMG) sensors) can be used to track real-time movement or pressure applied during a tendon stretch. Additionally, the sensor data can be stored in the model database 120. For example, the collected data can be used in modeling to assess muscle performance by comparing force output to known strength baselines. In some implementations, the collection of sensor data can include accessing data from a local storage unit of the sensor device 150 and/or receiving, via wireless communication, real-time sensor data. For example, the sensor devices 150 can be accessed by a mobile application (e.g., application 142) that synchronizes data for processing. In another example, the model system 110 can receive sensor data from the sensor devices 150 via a Bluetooth connection.

In some implementations, the model system 110 can be configured to determine at least one second result of the at least one muscle, ligament, or tendon test based at least on a predetermined threshold. The model system 110 can compare the collected sensor data to predefined thresholds (e.g., force output, joint stability, ligament flexibility, muscle endurance, and/or any range of motion limits) to generate the second result. That is, the model system 110 can analyze data such as force measurements, ligament flexibility, muscle activation patterns, joint movement against predetermined performance baselines (e.g., gender-specific averages, age-based strength baselines). For example, if the user performs a muscle strength test, the model system 110 can calculate a second result by comparing the measured force to the threshold values for muscle strength. Additionally, a plurality of the same tests can be performed such that the model system 110 can aggregate, weight, and/or average the multiple tests to generate a final result. That is, the model system 110 can use multiple trials to calculate an accurate representation of muscle performance. For example, the model system 110 can aggregate force output from three repetitions of a leg press test to determine average strength performance. In another example, the model system 110 can weigh the results of an endurance test to determine fatigue levels across multiple test sets. In some implementations, the model system 110 can aggregate data across multiple repetitions to determine an average result. Additionally, the second result can be generated based on performance trends (e.g., decreasing force over time, increasing flexibility, inconsistent muscle contractions) identified by a neural network. For example, the model system 110 can generate a second result indicating that the ligament stability of the user exceeds or falls short of the required threshold based on comparing the data of the user with the trained thresholds of the neural network for ligament strength.

In some implementations, the model system 110 can be configured to apply the at least one first result of the performance of the at least one mobility test, the at least one second result of the performance of the at least one muscle, ligament, or tendon test, the anatomy information, and the objective of the anatomy of the user as input to at least one second neural network to cause the at least one second neural network to generate at least one anatomy score corresponding with the anatomy of the user, and an anatomical conditioning protocol including at least a plurality of anatomy exercises. The model system 110 can use the second neural network to combine the results of the mobility and muscle tests (e.g., calf tests, hamstring tests, glut tests, quad tests, hip flexor tests, adductor tests, core tests, shoulder flexion tests, shoulder extension tests, should adduction tests, among other tests) with the anatomy information and objective to generate an overall anatomy score. That is, the second neural network can process the combined data and output an anatomy score representing the physical condition of the user. For example, the second neural network can receive the results of mobility and strength tests and output a biomechanical score that represents the joint health and muscle strength of the user. In some implementations, the neural network can also generate an anatomical conditioning protocol, recommending exercises and/or an exercise plan based on the score. Additionally, the conditioning protocol can include personalized exercises designed to improve the areas identified as weak or needing improvement. For example, if the anatomy score of the user indicates poor flexibility in the legs, the neural network can generate a conditioning protocol that includes targeted stretching exercises.

The system 100 can include at least one modeler 114. The modeler 114 can include any one or more artificial intelligence models (e.g., machine learning models, supervised models, neural network models, deep neural network models), rules, heuristics, algorithms, functions, or various combinations thereof to perform operations including anatomy score generation, conditioning protocol recommendations, or physical performance analysis, such as identifying mobility patterns or generating exercise plans. That is, a model can be a neural network trained to generate at least one anatomy score corresponding with the anatomy of the user. Additionally, the model can be a neural network trained to generate an anatomical conditioning protocol comprising at least a plurality of anatomy exercises. In some implementations, the model can include two or more neural networks such that each model can generate a unique output (e.g., a first model to generate at least one anatomy score corresponding with the anatomy of the user, and a second model to generate an anatomical conditioning protocol comprising at least a plurality of anatomy exercises). In some implementations, the modeler 114 can output results such as anatomy scores, conditioning plans, exercise recommendations, and/or any performance metrics (e.g., flexibility levels, strength improvement targets, injury risk factors). For example, the modeler 114 can output an exercise plan based on the anatomy score of the user. In another example, the modeler 114 can provide a risk assessment for specific injuries based on the physical profile of the user. In some implementations, the conditioning protocol can be provided to the user device 140 via the interface system 112 (e.g., as a visual display, in a mobile application (e.g., application 142), or downloadable plan).

In some implementations, the modeler 114 can maintain, execute, train, and/or update one or more machine-learning models during application of the at least one first result of the performance of the at least one mobility test, the at least one second result of the performance of the at least one muscle, ligament, or tendon test, the anatomy information, and/or objective of the anatomy of the user as input. In some implementations, the machine-learning model(s) can include any type of deep learning or reinforcement learning machine-learning models capable of processing results of various anatomical tests and other user data to generate anatomy scores, anatomy subscores, and conditioning protocols. For example, the machine-learning model(s) can be trained and/or updated to identify patterns in muscle strength, joint stability, and ligament flexibility, among other physical attributes. The machine-learning model(s) can be or include a transformer-based model (e.g., a generative pretrained transformer (GPT) model) designed to handle multimodal inputs for biomechanical analysis. The machine-learning model(s) can be or include a convolutional neural network (CNN) model, in some implementations. The modeler 114 can execute the machine-learning model to generate outputs. The modeler 114 can receive data to provide as input to the machine-learning model(s), which can include sensor data, video recordings, test results, anatomy scores, and/or any other data (e.g., generated by the modeler 114 and/or collected, received, and/or accessed by interface system 112).

The modeler 114 can include at least one neural network. The neural network can include an input layer, an output layer, and/or one or more intermediate layers, such as hidden layers, which can each have respective nodes. That is, the neural network can process the previously generated results of the mobility, muscle, ligament, or tendon tests. For example, the input layer can receive the first result of the mobility test and the second result of the muscle test as inputs. In another example, the output layer can generate an anatomy score and an anatomical conditioning protocol based on these inputs. In yet another example, the intermediate layers can process these results, comparing the test data against predefined thresholds and patterns learned from training data to identify potential areas of weakness or improvement. In some implementations, the training dataset 122 can be used to fine-tune the neural network to facilitate accurate predictions and recommendations based on the specific anatomy information of the user. That is, the training dataset 122 can contain data from previous users performing similar tests, allowing the neural network to identify trends and anomalies in the data of the user. For example, the training dataset 122 can include labeled results of mobility and strength tests.

In some implementations, the modeler 114 can configure (e.g., train, update, fine-tune, apply transfer learning to) the model by modifying or updating one or more parameters, such as weights and/or biases, of various nodes of the model responsive to evaluating the outputs of the model (e.g., generated in response to the results of the mobility, muscle, ligament, or tendon tests already performed). The modeler 114 can be or include various neural network models, including models that can operate on or generate data including but not limited to joint mobility, muscle strength, ligament flexibility, tendon elasticity, and/or various combinations thereof. For example, the modeler 114 can adjust the weights and biases of nodes within the neural network based on the performance of previous users in similar tests.

In some implementations, the modeler 114 can be configured (e.g., trained, updated, fine-tuned, has transfer learning performed, etc.) based at least on the training data of the at least one training dataset 122. For example, the at least one first result of the performance of the at least one mobility test, the at least one second result of the performance of the at least one muscle, ligament, or tendon test, the anatomy information, and objective of the anatomy of the user, and/or prior test results of similar users from the training data can be applied (e.g., by the modeler 114, or in a pre-training process performed by the modeler 114 or another system) as input to the modeler 114 to cause the modeler 114 to generate an anatomy score and an anatomical conditioning protocol (e.g., an output). The generated anatomy score can be evaluated and/or compared with baseline anatomy scores (or thresholds) of the training data that correspond with the one or more example sets of input data, such as mobility, strength, and flexibility test results. These inputs can be based on prior results from population-level datasets (e.g., gender-specific, age-specific, or activity-level baselines) and/or personalized user history (e.g., physical performance history, prior injuries). The model of the modeler 114 can be updated based at least on the evaluation of the current test results against these baseline thresholds. For example, based at least on an output of the mobility test of the user, one or more parameters (e.g., weights and/or biases) of the model of the modeler 114 can be updated to fine-tune the future predictions of the model for users with similar anatomical characteristics.

In some implementations, the model system 110 can be configured to provide the at least one anatomy score and the anatomical conditioning protocol. The model system 110 can output the generated score and protocol through the interface system 112. That is, the score and protocol can be transmitted to the user device 140 for display. For example, the model system 110 can provide the anatomy score and/or subscores of the user and the recommended conditioning exercises, through application 142. In some implementations, the score and/or subscore can be compared or otherwise benchmarked to baseline scores and/or subscores to provide an overall performance assessment. For example, an average soccer player can have 400 newtons of force in a hamstring such that a score of a user can be assessed relative to the baseline to determine muscle strength and resilience. In this example, the anatomy score can reveal that the hamstring strength of the user falls below this baseline, indicating a potential area for improvement. In another example, a user can have a joint stability score that surpasses the baseline values for their age group, suggesting a favorable condition (e.g., enhanced balance, reduced injury risk, increased mobility, and/or optimal alignment) for performance activities. In this example, the model system 110 can adjust the conditioning protocol to focus on maintaining or further improving stability while addressing any other identified weaknesses. That is, the favorable condition can be any condition indicating an improved and/or resilient anatomical profile supportive of high-intensity or repetitive activities.

In some implementations, the model system 110 can allow the user to view progress over time by comparing current anatomy scores with previously generated scores. Additionally, the conditioning protocol can be updated and provided after each assessment. For example, as the user progresses through the protocol, the model system 110 can update the exercise recommendations to adapt to improvements in the physical condition of the user.

In some implementations, the modeler 114 can be configured to generate a plurality of anatomy subscores corresponding to different regions or portions of the anatomy of the user. The subscores can be generated by applying the results of mobility tests, muscle strength tests, ligament flexibility tests, and tendon elasticity tests to various neural network layers that have been trained to assess localized performance metrics. That is, the neural network can be trained to process inputs from these anatomical tests and isolate specific regions (e.g., shoulders, hips, knees) based on predefined criteria or thresholds derived from the training dataset 122. For example, the input layer of the neural network can receive data related to joint flexibility, and the intermediate layers can determine subscores for specific regions by analyzing patterns in the range of motion and muscle control data. The output layer of the neural network can then generate anatomy subscores for each of these regions, indicating the health or performance level of the corresponding anatomical portion. The subscores can be outputted based on the anatomy information and objective of the user (e.g., focusing on knee flexibility or shoulder strength depending on the needs of the user).

The modeler 114 can refine the subscores further by incorporating data from previous users stored in the model database 120 to ensure that the subscores reflect broader population-level trends. For example, the neural network can use comparative data from users with similar physical profiles to adjust the weights and biases of the intermediate layers, ensuring that the subscores accurately reflect the anatomical condition of the user. In some implementations, the neural network can generate the anatomy subscores by aggregating data from multiple tests or by averaging scores across several repetitions of the same test. That is, the neural network can identify patterns in the sensor and multimedia data, and output subscores that provide a granular view of the physical health of the user, such as differentiating between strength in the left and right knees or between flexibility in the shoulders versus the hips. Additionally, the neural network can identify specific areas of improvement or concern based on discrepancies between the subscores and baseline values, which can then be incorporated into an anatomical conditioning protocol.

Generally, the model system 110 can be configured to interface (e.g., using the interface system 112) with a plurality of sensor devices 150 on a user or within a local network of a building (or commercial facility, or multi-unit complex) using protocols such as Bluetooth, Wi-Fi, or Ethernet. That is, the interface system 112 can process raw data streams from sensor devices 150 to provide input for mobility, strength, or flexibility analysis. For example, the interface system 112 can aggregate force measurements from multiple devices or synchronize video and sensor data for real-time analysis. In some implementations, the interface system 112 can control or coordinate the operation of a plurality of sensor devices 150 within a network based on one or more system-defined parameters, device configurations, user input, sensor-triggered events, or predefined conditions.

In some implementations, the interface system 112 can be configured to receive at least one transmission from a user device 140 and/or a sensor device 150 of a plurality of devices connected to network 130. That is, the interface system 112 can act as a data gateway, receiving packets of sensor data, video streams, or other inputs from multiple devices and forwarding this data to the modeler 114 for further processing. For example, the interface system 112 can receive sensor data from a pressure sensor capturing force applied during an exercise. In another example, the interface system 112 can receive motion data from a wearable sensor during a mobility test. In yet another example, the interface system 112 can receive video data from a camera capturing a specific test. That is, the interface system 112 can manage data transmission from multiple sources to facilitate synchronized processing. In some implementations, the interface system 112 can facilitate the receival by querying sensor devices 150 for periodic or event-based updates during test execution.

In some implementations, the sensor device(s) 150 can be another suitable computing system, for example, wearable fitness trackers, motion-capture devices, biomechanical sensors, gyroscopes, accelerometers, heart rate monitors, or within a single computer (e.g., a mobile device, tablet, or smartwatch). All such implementations are contemplated herein. The sensor device(s) 150 can include one or more local or remote processors, servers, transceivers, sensors, memory units, mobile devices, wearables, force sensors, pressure sensors, motion tracking units, GPS trackers, EMG sensors, optical sensors, smartwatches, smart rings, smart contact lenses, smart glasses, augmented reality glasses, virtual reality headsets, EEG sensors, mixed or extended reality glasses or headsets, and/or other electronic or electrical components, which can be in wired or wireless communication with one another.

In some implementations, the user device 140 can be another suitable computing system, for example, a smartphone, tablet, personal computer, laptop, or wearable device. All such implementations are contemplated herein. The user device 140 can include one or more local or remote processors, transceivers, memory units, mobile devices, graphical user interfaces, biometric sensors, accelerometers, gyroscopes, GPS modules, heart rate monitors, cameras, microphones, and/or other electronic or electrical components, which can be in wired or wireless communication with the sensor device(s) 150 and the model system 110. The user device 140 can be used to capture multimedia data (e.g., video, audio) during anatomical tests or to interact with the model system 110 to provide user input, monitor progress, and receive conditioning protocols.

In some implementations, the application 142 of the user device 140 can be a software program configured to interface with the model system 110 (e.g., interface system 112) and facilitate communication between the user and the model system 110. The application 142 can include one or more software packages or subsystems for capturing user input, transmitting test data (e.g., mobility test results, muscle strength data), monitoring user progress, and displaying anatomical conditioning protocols. The application 142 can use the hardware of the user device 140 (e.g., cameras, accelerometers, gyroscopes) to collect multimedia or sensor data during anatomical tests and transmit the data to the model system 110 for processing. In some implementations, the application 142 can integrate with various wearable devices (e.g., smartwatches, fitness trackers) to continuously collect performance metrics such as heart rate, force output, or motion tracking data. Additionally, the application 142 can provide real-time feedback, exercise recommendations, and performance monitoring to guide the user through the conditioning protocol. The application 142 can also store and display anatomy scores, subscores, and other user-specific information, allowing users to track their progress over time.

In some implementations, the modeler 114 can be configured to generate a prompt based on at least the anatomy information, the at least one first result of the at least one mobility test, and the at least one second result of the at least one muscle, ligament, or tendon test. The modeler 114 can process this input to generate a prompt by identifying one or more anatomical conditions of the user and the objective of the anatomy of the user. That is, the modeler 114 can analyze the received anatomy information and test results to identify anatomical issues and the desired outcomes of the user (e.g., rehabilitation, mitigation of injuries, strength improvement). For example, the modeler 114 can detect conditions such as ligament instability or muscle weakness and output a prompt that focuses on addressing these issues based on the specific objective of the user (e.g., injury prevention, recovery, flexibility enhancement). In some implementations, the modeler 114 can adjust the prompt generation process based on feedback or real-time data collected from sensor devices 150. Additionally, the modeler 114 can refine the prompt over time as more data is gathered from the user. For example, the modeler 114 can adjust the focus of the conditioning protocol based on updated anatomy information.

In some implementations, the modeler 114 can be configured to monitor the progress of the user performing the anatomical conditioning protocol based on at least one of receiving application data from a user device 140 or a third party, receiving an input via an interface system 112, and/or receiving an input from a sensor device 150 positioned to monitor the user or coupled to the user. The modeler 114 can track user progress by processing real-time or periodic data inputs from multiple sources, such as user device 140 and sensor devices 150. That is, the modeler 114 can assess how effectively the user is performing the prescribed exercises by receiving updates on exercise completion and performance metrics (e.g., repetitions completed, force output). For example, the modeler 114 can receive feedback from a smartwatch monitoring the heart rate of the user or movement patterns during a workout. In some implementations, the modeler 114 can adjust the conditioning protocol based on this progress data, such as by increasing or reducing exercise intensity. Additionally, the modeler 114 can interface with external applications to gather user-reported feedback or third-party assessments. For example, the modeler 114 can receive updates from a report of a physical therapist and adjust the conditioning protocol accordingly.

In some implementations, the modeler 114 can be configured to identify a context based at least on the objective of the anatomy of the user, wherein the context corresponds to one or more regions, muscles, ligaments, or tendons of the anatomy of the user. The modeler 114 can generate a context for the conditioning protocol by analyzing the specific anatomical goals of the user and identifying target areas for rehabilitation or development. That is, the modeler 114 can assess which specific muscles, ligaments, or tendons require focused attention based on the test results and the objectives of the user. For example, the modeler 114 can determine that a user aiming to rehabilitate a knee injury should focus on quadriceps and hamstring development to support knee stability. In some implementations, the modeler 114 can adjust the conditioning protocol by focusing on the targeted rehabilitation or strengthening of specific body regions. Additionally, the modeler 114 can use historical data from similar users to predict which anatomical regions will benefit most from particular exercises. For example, the modeler 114 can prioritize exercises aimed at improving shoulder mobility if the objective of the user is to recover from a shoulder injury.

In some implementations, the modeler 114 can be configured to apply the at least one first neural network to the set of multimedia or sensor data to analyze the at least one mobility test based at least on comparing a range of motion in the set of multimedia or sensor data to one or more predefined mobility thresholds. The modeler 114 can determine the at least one first result of the at least one mobility test based on the user meeting or exceeding the one or more predefined mobility thresholds. That is, the modeler 114 can process video or sensor data from the mobility test and compare it against known thresholds for joint range of motion and movement efficiency. For example, the modeler 114 can determine whether a knee flexion range of the user exceeds the normal mobility threshold of 120 degrees. In some implementations, the modeler 114 can analyze additional factors such as joint stability and fluidity of movement to refine the mobility test results. Additionally, the modeler 114 can cross-reference the data of the user (e.g., user data 124) with a baseline of expected performance.

In some implementations, the modeler 114 can be configured to determine at least one second result of the at least one muscle, ligament, or tendon test by aggregating and averaging a plurality of muscle, ligament, or tendon tests of at least one muscle, ligament, or tendon of the user. The modeler 114 can aggregate sensor data from multiple repetitions of the same test to produce an averaged result. That is, the modeler 114 can collect force or flexibility measurements from multiple instances of a muscle or tendon test and calculate a representative average for those measurements. For example, the modeler 114 can average the force output of a leg press of the user over five repetitions to determine the lower body strength of the user. In some implementations, the modeler 114 can weigh the results based on parameters, such as consistency of performance or variance in force output. Additionally, the modeler 114 can use the aggregated result to compare the strength or flexibility of the user to known baselines. For example, the modeler 114 can determine whether the average force output during a muscle strength test exceeds a threshold for healthy tendon performance. In another example, the modeler 114 can model the performance of the user against benchmarks from individuals in similar demographics with comparable physical characteristics (e.g., age, gender, weight, athletic activity level). That is, the assessment can identify deviations from the expected performance range, suggesting areas where conditioning or adjustments can be performed to align with typical standards for that demographic.

In some implementations, the modeler 114 can be configured to generate at least one updated anatomy score responsive to a predetermined schedule based on applying one or more updated results of performance of the at least one mobility test or the at least one muscle, ligament, or tendon test, the anatomy information, and the objective or an updated objective of the anatomy of the user as input to at least one second neural network. The modeler 114 can process updated test results on a scheduled basis to update the anatomy score and conditioning protocol of the user. For example, an individual of a certain age or demographic can have their updated anatomy score compared against age-based baseline averages to identify deviations or improvements in joint stability, flexibility, or muscle strength (e.g., knee stability rated on a 1-10 scale, shoulder mobility in degrees). In some implementations, a feedback or survey score can also be generated that measures subjective user feedback on progress and perceived improvement. That is, the modeler 114 can generate a feedback score by analyzing responses to a user survey on physical performance or comfort levels during exercise (e.g., a score out of 5 based on user ratings of joint comfort and flexibility). Additionally, the survey score can be generated by aggregating user responses to indicate overall satisfaction with the conditioning protocol (e.g., percentage satisfaction or improvement scores based on specific areas like endurance or mobility). In some implementations, a baseline can be updated and/or refined based on longitudinal performance data, reflecting changes over time in the anatomy score of the user and conditioning outcomes. For example, if an strength score of the individual consistently exceeds previous baselines, the modeler 114 can update the baseline upward to reflect improved capacity (e.g., recalibrating targets).

In some implementations, the modeler 114 can periodically analyze new test data, such as updated mobility or strength test results, and adjust the anatomy score of the user accordingly. For example, the modeler 114 can receive updated data from a follow-up muscle strength test and recalculate the overall biomechanical score of the user. In some implementations, the modeler 114 can adjust the conditioning protocol based on improvements or declines in the anatomy score. Additionally, the modeler 114 can compare the updated test results with the initial results of the user to track progress over time. For example, the modeler 114 can update the anatomy score to reflect increased leg strength and suggest a higher intensity conditioning protocol.

In some implementations, the modeler 114 can be configured to monitor the progress of the anatomical conditioning protocol based on receiving an indication of a performance by the user and determining the progress based on comparing the indication of the performance with at least one of the plurality of anatomy exercises. The modeler 114 can track the performance of the user and compare it to the prescribed exercises to assess progress. That is, the modeler 114 can receive data indicating exercise completion, such as repetitions performed or weights lifted, and compare it to the conditioning goals of the user. For example, the modeler 114 can compare the progress of the user in performing a stretching routine to the target range of motion for a specific joint. In some implementations, the modeler 114 can adjust the exercise regimen based on performance trends, such as increasing the intensity of the routine if the user exceeds expected thresholds. Additionally, the modeler 114 can cross-reference performance data with the initial conditioning protocol to identify areas where further adjustments can be required. For example, the modeler 114 can reduce the intensity of the exercises if the user reports difficulty in completing the routine.

Referring now to FIG. 2, a flowchart for a method 200 for anatomical and injury modeling, in accordance with present implementations. At least the example system 100 can perform method 200 according to present implementations.

In broad overview of method 200, at block 210, the one or more processing circuits (e.g., model system 110) can receive a request including anatomy information of a user. At block 220, the one or more processing circuits can determine or identify a plurality of anatomical tests to be performed by the user. At block 230, the one or more processing circuits can collect, from at least one camera or sensor, a set of multimedia or sensor data of a performance of at least one mobility test. At block 240, the one or more processing circuits can apply the set of multimedia or sensor data as input to at least one first neural network to cause the at least one first neural network to generate at least one first result of the at least one mobility test. At block 250, the one or more processing circuits can collect, from at least one sensor, sensor data during performance of at least one muscle, ligament, or tendon test. At block 260, the one or more processing circuits can determine at least one second result of the at least one muscle, ligament, or tendon test based at least on a predetermined threshold. At block 270, the one or more processing circuits can apply the at least one first result of the performance of the at least one mobility test, the at least one second result of the performance of the at least one muscle, ligament, or tendon test, as input to at least one second neural network to cause the at least one second neural network to generate (i) at least one anatomy score corresponding with the anatomy of the user, and (ii) an anatomical conditioning protocol. At block 280, the one or more processing circuits can provide the at least one anatomy score and the anatomical conditioning protocol. Additional, fewer, or different operations can be performed depending on the particular implementation. In some implementations, some, or all operations of method 200 can be performed by one or more processors executing on one or more computing devices, systems, or servers. In various implementations, each operation can be re-ordered, added, removed, or repeated.

Referring to method 200 generally, the method 200 can include receiving anatomy information, processing data from anatomical tests, applying neural networks, generating results, and/or any combination thereof. The method 200 can further include updating conditioning protocols based on feedback. That is, the processing circuits collect and analyze data from multiple sources, integrating the results to output recommendations. In some implementations, the method 200 aggregates data from multimedia sensors and generates and/or updates protocols based on detected weaknesses or risks. Additionally, method 200 provides improvements over traditional systems that rely on manual assessments and generalized protocols. Systems and methods often encounter technical problems related to incomplete data collection and limited capabilities for adapting to inputs. That is, conventional methods process data in a static manner without incorporating dynamic adjustments. Method 200 addresses these issues by applying machine learning models that generate and/or update conditioning protocols based on test results and predictive injury analysis.

At block 210, the one or more processing circuits can receive a request (e.g., client intake) including anatomy information (e.g., height, weight, sports activities, right or left handed, goals, treating an injury or not, specific injury, age, sex, and/or any relevant medical history) of a user and an objective (e.g., injury, treatment, general improvement) of an anatomy of the user. The request can be a form or input provided through an interface that can include fields for various user details. That is, the processing circuits can process the received information to determine specific user needs. The anatomy information can include physical attributes, past injuries, medical conditions, current fitness level, specific mobility concerns, and/or any other relevant data. For example, the request can be submitted through a user portal, which can include relevant anatomy information (e.g., the medical history of the user and athletic background).

In some implementations, the user can indicate an objective, such as injury recovery, strength training, flexibility improvement, or general physical conditioning. For example, a user can be aiming to recover from an ACL tear and/or reduce the likelihood of an ACL tear occurring in the future. Additionally, the request can include background information of the user such as the particular sport or sports the user plays, the level of competition, training frequency, and/or any specific performance goals. In some implementations, the request can be submitted through a web interface or mobile application configured to collect and transmit user data securely. For example, the user can enter their details via a smartphone app.

At block 220, the one or more processing circuits can determine or identify a plurality of anatomical tests (e.g., mobility tests, muscle tests, balance test, and/or any functional performance tests) to be performed by the user. The determination can be based on the anatomy information, user objectives, past medical history, user age, and/or any physical limitations. That is, the processing circuits can analyze the user-provided information, identify potential areas of weakness or concern (or determine a general assessment should be performed), and/or determine the suitable tests. For example, the processing circuits can determine that a specific set of muscle strength tests should be performed based on a history of knee injuries. In some implementations, the plurality of tests can include dynamic movement assessments, strength evaluations, and/or joint flexibility tests.

In some implementations, the processing circuits can prioritize tests based on specific risk factors, such as past injuries, sports-specific requirements, and physical imbalances. That is, the determination can further include analyzing data patterns from similar users to identify relevant anatomical tests. For example, the processing circuits can identify and/or analyze historical data related to athletes of a similar age and activity level to identify tests most correlated with obtaining baseline anatomical performance metrics (e.g., strength tests, flexibility tests, joint stability tests). In this example, the processing circuits can select specific tests to measure (e.g., quadriceps strength, hamstring flexibility, knee joint stability). That is, the tests can be chosen to collect data to assess the current physical condition of the user and identify potential areas of concern (e.g., muscle imbalances, joint instability, flexibility limitations). In some implementations, the processing circuits can update test parameters, adjust testing protocols, and/or refine the test selection process to determine one or more effective assessment methods.

In some implementations, the anatomical tests can be selected from a group of pre-defined groups of tests. That is, the processing circuits can analyze the information of the user and match it with a predefined set of tests designed for different types of users (e.g., based on sports activities or specific injuries). For example, a group of mobility tests designed for runners can be selected if the user indicates that they regularly engage in running activities. In another example, strength and balance tests for users recovering from knee injuries can be identified based on user-provided medical history. Additionally, the anatomical tests can be standardized across different sports or activity types such that consistent evaluation metrics can be applied. For example, joint flexibility tests can be standardized for athletes in both swimming and gymnastics to facilitate uniformity in data comparison.

In some implementations, identifying the anatomical tests can include identifying predefined risk categories and corresponding test protocols. That is, the processing circuits can categorize users into groups based on baseline needs and assign corresponding anatomical tests (e.g., ligament strength tests, muscle endurance assessments). For example, a user with a history of ligament injuries can be assigned tests to measure baseline metrics (e.g., ACL strength, joint flexibility, ligament stability). In another example, users with a history of muscle strains can be directed to assessments measuring baseline data for (e.g., muscle endurance, recovery capacity, muscle flexibility).

At block 230, the one or more processing circuits can collect a set of multimedia or sensor data of a performance of at least one mobility test of the plurality of anatomical tests performed by the user. The collection can be from at least one camera or sensor (e.g., smartphone camera, depth-sensing camera, wearable sensor, motion sensor). That is, a mobile device can be used to record the performance of the user during the test. For example, a camera of the mobile device can be used to capture video footage, and the processing circuits can collect visual data for motion analysis. In another example, an accelerometer sensor of the mobile device can be used to track movement, and the processing circuits can collect acceleration and velocity data. That is, the processing circuits can collect visual or motion data from the performance of the test by the user.

In some implementations, the multimedia or sensor data can include video footage, accelerometer data, gyroscopic data, motion tracking, and/or any other sensor inputs. For example, the processing circuits can use a depth-sensing camera to record the range of motion during a knee flexion test. Additionally, the processing circuits can collect data related to limb movement, joint angles, and/or muscle activation during the test. In some implementations, motion tracking algorithms (e.g., optical flow, skeletal tracking, kinematic analysis) can be applied to facilitate the capture of biomechanical data.

At block 240, the one or more processing circuits can apply the set of multimedia or sensor data as input to at least one first neural network (e.g., vision model, motion tracking model, posture analysis model) to cause the at least one first neural network to generate at least one first result of the at least one mobility test (e.g., pass/fail result, range of motion result, joint stability score, and/or any movement quality metric). That is, the processing circuits use the neural network to analyze the collected data and output a quantified result. For example, the vision model can evaluate joint alignment during the test and assign a pass or fail result based on predefined thresholds (e.g., joint angle deviations, range of motion limits, stability thresholds).

In some implementations, a vision model can be implemented using convolutional layers to detect body pose and skeletal structure. That is, the processing circuits extract and process visual data to evaluate movement characteristics in real-time. For example, in causing the vision model to generate mobility test results, the processing circuits can extract frame-by-frame motion data to assess movement fluidity (e.g., of knee flexion, shoulder abduction, hip rotation). The at least one first result can include range of motion analysis, joint stability scores, and/or overall movement efficiency ratings.

Generally, the vision model can be a convolutional neural network (CNN), a 3D pose estimation model, recurrent neural network (RNN), transformer-based model, any deep learning architecture suitable for visual data analysis, and/or any deep learning model designed for motion and biomechanical analysis. A vision model can be trained on motion capture data that includes labeled joint positions and movements to recognize anatomical landmarks (e.g., right ankle, knee, hip) and assess joint mobility. For example, the vision model can be trained by using a dataset of individuals performing mobility tests, where, for example the range of the right ankle of motion is annotated in terms of dorsiflexion, plantarflexion, inversion, and/or eversion angles. In this example, the vision model can learn (be trained) to predict joint angles by identifying points on the foot, leg, and/or other body portions and analyzing how these points move relative to each other, and comparing them to expected behavior for a given movement.

For example, in assessing whether the right ankle passes a mobility test, the vision model can receive video input where the user performs a specific movement such as ankle dorsiflexion or plantarflexion. The vison model can first detect and map anatomical landmarks on the foot and lower leg, such as the heel, ankle joint, and toes. These landmarks can be tracked frame by frame, allowing the vision model to estimate the angles of movement during the test. For example, the model can calculate the dorsiflexion angle by measuring the difference between the angle formed by the tibia (shinbone) and the top of the foot during the movement. In this example, the vision model can compare the measured dorsiflexion angle to predefined thresholds. If the angle exceeds the minimum required threshold (e.g., 20 degrees of dorsiflexion for normal mobility), the model can classify the result as a pass. If the angle falls below this threshold, the result can be classified as a fail. Additionally, the model can account for other criteria such as smoothness of movement and joint stability by analyzing how consistently the ankle moves through the range of motion without unnecessary lateral movement or compensatory actions from adjacent joints. That is, the vision model can be used to assess both the range of motion and the quality of the movement.

In some implementations, the vision model can be configured to (e.g., trained and implemented to) detect signs of instability by tracking, for example, whether the ankle (or other body portions) moves laterally or exhibits excessive wobbling during the movement. This is done by comparing the relative motion of the ankle joint with the knee and hip joints to detect any compensatory or irregular movement patterns. The vision model can identify and/or flag any such patterns, indicating potential weakness or imbalance in the ankle or surrounding muscles. The output of the model can be a pass/fail classification, along with quantitative data on the range of motion, stability, and any detected abnormalities of, for example, the right ankle.

In some implementations, the at least one first neural network can be applied to the set of multimedia or sensor data to analyze the at least one mobility test. For example, the mobility score can be a pass-fail test (e.g., given by a doctor, trainer, or other third-parties) determined by the neural network and/or a score (e.g., on a scale of 1-5, 1-10, 1-100, using movement range, joint stability, and/or coordination). That is, the neural network can be a vision model trained to analyze motion sequences for joint mechanics and alignment. For example, an image can be captured and the vision model can receive the image as input to determine joint positions and output a score (e.g., 1-100, 1-10, pass/fail) indicative of overall mobility. The analysis can be based on comparing a range of motion (e.g. of the user) in the set of multimedia or sensor data to one or more predefined mobility thresholds (e.g., joint angles, movement speed, muscle activation, and/or any mechanical criteria). That is, the range of motion can be compared to baseline averages, and the predefined mobility thresholds can be derived from population data. For example, a knee flexion angle exceeding a certain degree can indicate above-average flexibility. In another example, a low score can indicate limited mobility but does not trigger further action, as it is part of the baseline assessment.

In some implementations, the at least one first neural network can be applied to the set of multimedia or sensor data to further determine the at least one first result of the at least one mobility test based on the user meeting or exceeding the one or more predefined mobility thresholds (e.g., range of motion, muscle control, stability, and/or any biomechanical measure). That is, the processing circuits can classify the movement patterns of the user based on the thresholds to establish a baseline. For example, a high score can indicate optimal (or improved or ideal) joint and/or body health, while a low score establishes baseline limitations for future reference.

Additionally, at block 240, the processing circuits can generate at least one first result of the at least one mobility test based on the set of multimedia or sensor data. That is, the processing circuits can analyze the performance data collected from the user, processing specific details such as range of motion, joint stability, and coordination, to output a quantified result for the mobility test. For example, the processing circuits can classify the performance of the user in relation to predefined standards (e.g., mobility thresholds, stability metrics, range of motion baselines). In some implementations, the processing circuits can compare movement data associated with the user to stored baseline values, identifying any deviations from standard or expected ranges. Additionally, the first result can include a pass/fail outcome, range score, or movement efficiency rating that reflects baseline capabilities of the user. For example, if joint stability falls within acceptable limits, the processing circuits can assign a passing score, whereas an outlier could indicate the need for further monitoring or future assessment. In some implementations, the processing circuits can refine results by referencing aggregated data from similar assessments, ensuring the generated result aligns with expected movement baselines and industry standards.

For example, the processing circuits can analyze data from a shoulder abduction test and generate a movement efficiency score based on smoothness and range of motion. In this example, the movement efficiency score can be generated by calculating the average speed of shoulder abduction, the peak angle achieved, and any observed deviations in the movement trajectory, with each parameter weighted to produce a combined efficiency metric (e.g., score on a scale of 0-100). In another example, the processing circuits can calculate a joint stability rating by examining knee flexion data, comparing flexion angles and movement speed against predefined stability metrics. In this example, the joint stability rating can be generated by quantifying lateral deviations during flexion, calculating the time taken to achieve maximum flexion angle, and assessing the variance in flexion angles across multiple repetitions, producing a stability score (e.g., pass/fail or a 1-10 stability rating). Additionally, during a balance test, the processing circuits can evaluate balance stability by analyzing sway metrics captured by motion sensors, generating a score that indicates the baseline balance ability of the user. In this example, the balance stability score can be generated by measuring sway range in millimeters, the frequency of sways per second, and deviations from a central stance position, with results aggregated into a balance index (e.g., balance score out of 100). In yet another example, the processing circuits can use ankle dorsiflexion data to generate a flexibility score. In this example, the flexibility score can be calculated by measuring the maximum dorsiflexion angle achieved in degrees, the consistency of the angle across multiple trials, and comparing it against baseline population data, resulting in a flexibility rating (e.g., on a 1-5 scale or percentage of baseline flexibility).

At block 250, the one or more processing circuits can collect sensor data during performance of at least one muscle, ligament, or tendon test of the plurality of anatomical tests performed by the user. The various tests can be measured in Newtons of force, pressure thresholds, and/or degrees of flexibility. In some implementations, calisthenic exercise can be performed such that sensor data (e.g., videos, images, motion tracking, pressure sensors) can indicate muscle strength or joint stability. For example, a push-up test can collect data on upper body strength. Additionally, a smart watch can be used to collect sensor data (e.g., velocity data, force applied, joint angle) from such that wrist movement and heart rate data are recorded during testing. For example, sensor data from the watch can reveal decreased wrist stability during a particular exercise. That is, the sensor data can be collected from at least one sensor (e.g., pressure sensors, strain gauges, accelerometers, gyroscopes, and/or any wearable device). The collected data can include force measurements, joint stability data, flexibility measurements, velocity data, and/or any physical metric related to muscle or ligament performance. For example, pressure sensors can record force applied during a squatting exercise. In some implementations, performance of at least one muscle, ligament, or tendon test can include resistance exercises or flexibility tests.

In some implementations, the sensor data collected from these tests will be used to establish a baseline profile of the muscle, ligament, or tendon performance of the user. For example, performance of a muscle test can include measuring baseline force production during resistance exercises such as weight lifting. In another example, performance of a ligament test can include measuring the baseline elasticity of ligaments under normal conditions. In yet another example, performance of a tendon test can include measuring the baseline stretch of tendons under stress. That is, collecting data from the various tests can be used to establish an initial (or updated) physical condition of the user.

At block 260, the one or more processing circuits can determine at least one second result (e.g., aggregating and/or averaging a plurality of results) of the at least one muscle, ligament, or tendon test based at least on a predetermined threshold. That is, determining can include comparing force output across multiple tests to identify patterns or weaknesses. For example, the processing circuits can analyze the collected data and calculate an average muscle strength value. In this example, three muscle tests can be performed by the user on the right calf, where each test can output a Newtons of force measuring muscle exertion. Further in this example, the processing circuits can aggregate these measurements and compare them against baseline strength data. In still this example, five muscle tests can be performed by the user on the left hip flexor, where each test can output a Newtons of force measuring overall strength under load.

Further in this example, the processing circuits can average the data points and identify any discrepancies in strength between limbs.

In some implementations, the predetermined threshold can be based on standard ranges of force for the tested muscles, ligaments, or tendons. For example, the threshold can be set according to age and gender-specific averages for muscle output. In another example, the threshold can be customized based on the specific goals of the user (e.g., injury recovery, maintaining current physical condition, establishing initial fitness levels). In some implementations, the processing circuits can identify patterns in the data to establish baseline (or updated) metrics for future comparisons.

In some implementations, the processing circuits can determine the at least one second result of the at least one muscle, ligament, or tendon test can include aggregating and averaging a plurality of muscle, ligament, or tendon tests of at least one muscle, ligament, or tendon of the user. That is, the processing circuits can aggregate multiple test results into a single summary metric. For example, if three separate tests measure different aspects of knee ligament strength, the processing circuits can combine those measurements to generate an overall score for knee health. In another example, multiple muscle tests on the upper and lower body can be combined to identify overall muscle strength balance.

In some implementations, the sensor data can include one or more force measurements (e.g., Newtons of force) from the at least one sensor positioned to monitor at least one muscle, ligament, or tendon corresponding with the at least one muscle, ligament, or tendon test. That is, the processing circuits can calculate force exertion during the test and compare it against predefined thresholds to determine whether the muscle or ligament performance of the user is within acceptable ranges. For example, the system can determine that the calf muscles of the user exerted a force within 10% of the expected value for their age and weight.

In some implementations, the processing circuits can generate a prompt (e.g., for the second neural network) based on at least the anatomy information, the at least one first result of the at least one mobility test, and/or the at least one second result of the at least one muscle, ligament, or tendon test. That is, the prompt can include data points such as strength, mobility, and overall performance, facilitating the generation of a conditioning protocol and anatomy score by the neural network. Additionally, generating the prompt can include identifying one or more anatomical conditions of the user and the objective of the anatomy of the user. In some implementations, an anatomical condition can be muscle weakness, ligament instability, joint stiffness, imbalance, and/or any other factor impacting mobility or strength. That is, the prompt can include various factors to model. In some implementations, the objective of the anatomy of the user can be establishing a baseline for rehabilitation, strength assessment, flexibility measurement, injury risk profiling, and/or balance testing. That is, the prompt can include data points that can be used to establish baseline anatomical conditions and performance metrics, to be processed by the model.

At block 270, the one or more processing circuits can apply (e.g., as an input) the at least one first result of the performance of the at least one mobility test, the at least one second result of the performance of the at least one muscle, ligament, or tendon test, the anatomy information, and/or objective of the anatomy of the user as input to at least one second neural network to cause the at least one second neural network to generate (e.g., as an output) (i) at least one anatomy score (e.g., overall bio-mechanical optimum output score) corresponding with the anatomy of the user, and (ii) an anatomical conditioning protocol (e.g., an improvement and/or rehab plan) including at least a plurality of anatomy exercises (e.g., various scheduled exercises). That is, applying can include feeding the test results and anatomy information as feature vectors into the neural network layers, where each layer processes aspects of the data (e.g., mobility, strength, stability) to generate an output. For example, the processing circuits can encode the mobility test results into a multidimensional vector that represents joint angles, movement efficiency, and range of motion, which can then be processed by the model to determine overall biomechanical performance.

In some implementations, causing can include configuring the model to adjust its internal parameters based on the test data to generate anatomy scores for the user. For example, the processing circuits can input force measurements, joint flexibility, and tendon elasticity data into the model, which processes these inputs through trained layers (e.g., convolutional, recurrent) to generate a numerical anatomy score representing overall physical condition. The at least one second result can include the anatomy score which can include joint stability, muscle strength, flexibility range, and overall mobility based on the baseline data of the user and predefined thresholds. For example, an anatomy score can be a numerical value ranging from 0 to 100, representing the bio-mechanical condition of the user across different anatomical regions, such as legs, arms, and core. The at least one second result can include the conditioning protocol which can include exercise recommendations based on the anatomy score, focusing on areas of improvement or maintenance. For example, a conditioning protocol can be structured with specific exercises targeting flexibility, strength training, joint stability, muscle endurance, and/or recovery exercises, tailored to the baseline scores obtained from the tests by the user.

Generally, the second neural network can be a fully connected feedforward neural network, a recurrent neural network (RNN), a transformer-based model, or any deep learning architecture trained and implemented to process numerical and categorical data for biomechanical analysis. The second neural network can be trained on datasets that include labeled anatomy scores and conditioning protocols, correlating physical performance metrics (e.g., range of motion, muscle strength, joint stability) with specific anatomical outcomes. For example, the second neural network can be trained using data from individuals who have completed both mobility and muscle strength tests, where at least one (e.g., each) test result is annotated with corresponding anatomy scores and conditioning recommendations. In this example, the second neural network can be trained to predict overall anatomy scores by analyzing the relationship between the mobility and muscle test results and the corresponding conditioning protocol recommendations, and applying learned patterns to generate outputs for new inputs.

For example, in generating an anatomy score for a user, the second neural network can receive input data including mobility test results (e.g., joint flexibility, movement efficiency) and muscle strength test results (e.g., Newtons of force, endurance capacity). The second neural network can process these inputs through its hidden layers, each of which can be responsible for extracting specific features from the input data, such as joint stability or muscle performance.

These features can be aggregated into a representation of the biomechanical health of the user. For example, the neural network can calculate an anatomy score by assigning weighted values to each input, such as prioritizing joint stability in users with a history of ligament injuries. The neural network can also compare the generated anatomy score to predefined thresholds. If the score meets or exceeds the baseline threshold for a given anatomical region (e.g., right knee, left hip), the neural network can classify the anatomy as optimal (or improved, or ideal), for example. If the score falls below the threshold, the neural network can flag the region for potential further assessment. Additionally, the second neural network can generate subscores for specific body regions.

In some implementations, the at least one anatomy score can include a plurality of anatomy subscores corresponding with a plurality of regions or portions of the anatomy of the user. That is, the processing circuits can determine the anatomy subscores of specific body regions (e.g., shoulders, hips, knees) by processing the test results through neural network layers trained to assess localized performance metrics. For example, the processing circuits can pass mobility test data and force measurements through region-specific neural network layers trained to evaluate joint flexibility and muscle strength. In some implementations, a subscore can be generated for the mobility tests, the at least one muscle, ligament, or tendon test, and/or other performance (e.g., broad jump, balance test, lateral movement test, and/or any other biomechanical measure). The subscores can be one or more indicators, such as but not limited to, above average/average/below average with corresponding colors (e.g., green for above average, yellow for average, and red for below average), exceeds/satisfies/needs improvement with corresponding labels, 5/4/3/2/1 with corresponding numerical values (e.g., 5 for excellent, 3 for average, 1 for needs improvement), percentile scores with corresponding ranges (e.g., top 10%, 50th percentile, bottom 20%), threshold-based indicators with corresponding warnings (e.g., low mobility warning, muscle imbalance alert, joint instability risk), and/or any other categorical rating. For example, a subscore can reflect knee joint flexibility or shoulder stability, based on thresholds learned during the training of the neural network on population-level data.

In some implementations, the anatomy score can also include subscores for portions or regions of the body (e.g., right shoulder, left shoulder, right arm, left arm, right knee, left knee, right thigh, left thigh, abdominals, right calf, left calf, lower back, upper back, neck, and/or any other part of the anatomy). That is, at least one subscore for portions or regions of the body can also be associated with one or more indicators, such as but not limited to, good/mild/at risk with corresponding colors (e.g., green for good, yellow for mild, and red for at risk), percentile-based categories with corresponding ranges (e.g., top 10%, middle 50%, bottom 25%), risk factor thresholds with corresponding labels (e.g., low flexibility, high injury risk, moderate stability), neural network-derived predictions with corresponding warnings (e.g., ligament strain risk, reduced mobility potential, muscle fatigue warning), and/or any similar classification.

In some implementations, the anatomical conditioning protocol can include an exercise or recovery routine corresponding with a frequency (e.g., every day, every other day, every week) and duration (e.g., 2 weeks, 4 weeks, 6 weeks) of at least one of the plurality of anatomy exercises. That is, the processing circuits can process the anatomy scores and subscores as inputs to the second neural network to generate a baseline exercise and/or recovery routine targeting specific muscle groups or anatomical regions. For example, the neural network can assign exercise types and durations based on patterns identified in the test results of the user and compared to baseline data from similar users (e.g., individuals with similar joint stability issues, similar muscle strength profiles, or similar flexibility limitations). In this example, the second neural network can evaluate the knee joint stability of the user and compare it to the baseline data from similar users to recommend a set of exercises designed to improve knee strength and stability. That is, the frequency can be every other day and the duration can be 4 weeks.

In some implementations, the processing circuits can receive performance data of the user (e.g., monitoring performance of the anatomical conditioning protocol, such as the exercises being performed). For example, the processing circuits can monitor sensor data from wearables or motion tracking devices during each workout and use this data as input to the neural network to assess the progress of the user (e.g., where the neural network can analyze performance metrics such as force exertion, joint mobility, and exercise completion rates). In some implementations, the processing circuits can update the exercise and/or recovery routine based at least on the performance data. That is, the processing circuits can adjust the number of repetitions, intensity, or frequency of the exercises by processing the updated data through the neural network. That is, processing can include the neural network analyzing sequential performance data by using temporal data analysis techniques (e.g., recurrent neural networks or long short-term memory (LSTM) layers) to capture trends in strength or flexibility over time.

In some implementations, the neural network can detect changes in the data such as increased range of motion or higher force output, using weights and biases adjusted during training to predict whether the performance of the user is improving or stagnating. The neural network can compare current data points (e.g., joint angles, force production, and endurance) against past performance metrics. For example, the neural network can use backpropagation through time (BPTT) to update the internal parameters of the neural network based on patterns of improvement or plateauing, and generate updated recommendations for exercise adjustments accordingly. Additionally, in another example, if the progress of the user exceeds predefined thresholds, the neural network can increase the difficulty of the exercise regimen. In yet another example, if the user demonstrates slower progress, the neural network can adjust the exercises by recommending a lower intensity or different types of exercises In some implementations, the output of the model can include particular weights and number of reps to complete during one or more exercise and/or recovery routines. For example, the output of the model can be customized to a first individual that demonstrates strong lower body mobility but weak upper body flexibility. In this example, the model can recommend a higher number of reps for upper body flexibility exercises. In another example, the output of the model can be customized to a second individual that demonstrates balanced strength but poor endurance. In this example, the model can focus on endurance-building exercises with moderate weights and higher repetition counts. Thus, method 200 provides various technical improvements to the generation and optimization of exercise and/or recovery routines by utilizing a neural network that dynamically adjusts the conditioning protocol based on real-time performance data and biomechanical modeling. The neural network can incorporate multi-modal inputs (e.g., force measurements, joint angle tracking, and velocity data) and use predictive modeling to identify micro-adjustments in exercise form and intensity. By applying data processing layers (e.g., convolutional layers for spatial data and recurrent layers for time-series data), the processing circuits can predict the optimal (or improved, or ideal) progression of exercise load and volume tailored to the unique anatomy of the user and performance over time. This technical improvement facilitates the conditioning protocol to be continuously refined to account for both immediate feedback and long-term trends, thus increasing the effectiveness of the program while reducing the risk of injury or overtraining.

At block 280, the one or more processing circuits can provide (e.g., on a graphical user interface) the at least one anatomy score and the anatomical conditioning protocol (e.g., present the score and provide the exercise plan). That is, providing can include displaying the score and protocol in a format that allows the user to track their progress. For example, the processing circuits can generate a graphical dashboard depicting anatomy subscores and exercise recommendations. In another example, the processing circuits can provide the user with a weekly progress report identifying changes in their anatomy scores and suggesting modifications to the exercise plan.

In some implementations, method 200 can further include the processing circuits monitoring a progress of the anatomical conditioning protocol. For example, monitoring the progress can include receiving an indication of a performance by the user and/or determining the progress based at least on comparing the indication of the performance with at least one of the plurality of anatomy exercises. That is, receiving an indication of a performance by the user can include collecting data from wearable sensors or manual user input. For example, the user can input whether they completed the assigned exercises, and the processing circuits can update the protocol based on this input In some implementations, determining the progress can include analyzing changes in the anatomy scores of the user over time. For example, the processing circuits can compare the initial scores of the user with their current scores to measure improvement. In some implementations, the anatomical conditioning protocol can progress by gradually increasing exercise intensity or frequency. That is, the processing circuits can monitor the progress by adjusting the difficulty of exercises based on user performance data. For example, the processing circuits can recommend increasing weights or reps as the strength improves of the user. That is, monitoring the progress can include collecting real-time sensor data (e.g., force output, joint angles, movement velocity) and/or receiving user-inputted feedback on exercise completion and perceived exertion. For example, the processing circuits can gather accelerometer and gyroscope data from wearable devices to monitor movement speed and joint stability during exercises and track user-reported feedback on fatigue levels after each workout.

In some implementations, method 200 can further include the processing circuits generating a graphical user interface (GUI). The GUI can include an anatomical outline (e.g., a visual representation of the body of the user) of the anatomy of the user. The GUI can be interactive, customizable, and display user-specific data. That is, the anatomical outline can include at least one indicator (e.g., color-coded sections, numerical values, progress bars) corresponding to at least one of the plurality of regions or portions of the anatomy of the user (e.g., shoulders, knees, hips, elbows, etc.). For example, the GUI can display a red indicator over the knee of the user to highlight an area at risk. In some implementations, the at least one indicator can represent a prediction of a future condition of at least one of the plurality of regions or portions of the anatomy of the user based at least on a corresponding anatomy subscore of the plurality of anatomy subscores. That is, the processing circuits can predict potential injury risks based on current scores. For example, if a knee subscore of the users shows weakness, the processing circuits can predict a higher likelihood of knee-related issues in the future. In another example, the processing circuits can recommend preventive exercises to strengthen the knee and reduce the risk of injury (e.g., in the anatomical conditioning protocol).

In some implementations, method 200 can further include the processing circuits providing a GUI including the at least one indicator, the at least one anatomy score, and the plurality of anatomy subscores. That is, the GUI can include interactive elements that allow the user to explore their scores and subscores in detail. For example, the GUI can display anatomy scores for different parts of the body, such as legs, arms, and core strength. Additionally, at least one (e.g., each) of the plurality of anatomy subscores can correspond to at least one of the plurality of regions or portions of the anatomy of the user. That is, the subscores can be visually linked to specific body parts, allowing the user to identify areas for improvement. For example, a subscore for the left knee of the user can show a "needs improvement" rating, prompting the user to focus on strengthening that area (e.g., by following the anatomical conditioning protocol). In another example, the right shoulder of the user can have a "good" rating, indicating that no immediate attention is needed (e.g., as represented/not represented in the anatomical conditioning protocol).

In some implementations, at least one indicator can categorize at least one (e.g., each) of the plurality of regions or portions into a first category representing a favorable condition (e.g., strong, flexible, stable), a second category representing a mild condition (e.g., minor weakness, slight stiffness), and a third category representing an at-risk condition (e.g., unstable, prone to injury) based at least on the corresponding anatomy subscore. That is, the processing circuits can categorize at least one (e.g., each) body region based on the subscores, providing targeted feedback. For example, the first category can be displayed as green for body regions with strong performance. In this example, green regions can indicate that no corrective actions are needed. In another example, the second category can be displayed as yellow for regions that need mild improvement. In this example, yellow regions can prompt the user to perform additional exercises (e.g., as provided in the anatomical conditioning protocol). In yet another example, the third category can be displayed as red for regions at risk of injury. In this example, red regions signal the need for immediate attention (e.g., as indicated in the anatomical conditioning protocol).

In some implementations, method 200 can further include the processing circuits monitoring a progress of the user performing the anatomical conditioning protocol. That is, the processing circuits can track user compliance and improvement over time. For example, the progress of the user performing the anatomical conditioning protocol can include the processing circuits receiving application data (e.g., exercise completion, performance metrics, feedback) of a user device of the user or a third-party. In this example, the processing circuits can receive the data by syncing with the mobile application or fitness tracker through a wireless connection (e.g., Bluetooth, Wi-Fi).

In another example, the progress of the user performing the anatomical conditioning protocol can include the processing circuits receiving, via an interface (e.g., application programming interface (API), mobile app, website), an input (e.g., exercise completion status, feedback, new goals) from the user or the third-party. In this example, the processing circuits can receive the input by querying the API or receiving real-time updates through the user interface of the mobile app or website.

In yet another example, the progress of the user performing the anatomical conditioning protocol can include the processing circuits receiving an input from a sensor device (e.g., smart watch, sensor on a particular exercise machine or device (e.g., treadmill), pressure sensor, and/or any wearable device) positioned to monitor the user (e.g., movement, exercise intensity, recovery progress) or coupled to the user (e.g., heart rate monitor, step counter, force sensor). In this example, the processing circuits can gather data from the physical activity of the user by capturing real-time sensor data (e.g., step count, force applied, or heart rate variability).

In some implementations, method 200 can further include the processing circuits identifying a context based at least on the objective of the anatomy of the user. That is, the context can correspond to one or more regions, muscles, ligaments, or tendons of the anatomy of the user and can be determined based on the performance data of the user and anatomical goals. For example, the context can be associated with improving leg strength for a runner. In this example, the processing circuits can identify the context by analyzing the initial intake data provided by the user, such as injury history, primary sport or activity (e.g., running), and specific goals (e.g., increase leg strength to avoid injury). The processing circuits can further refine the context by incorporating performance data from initial baseline tests (e.g., mobility and strength assessments) to confirm that the identified anatomical regions (e.g., quadriceps, hamstrings) are relevant to the objective of the user in improving performance and preventing injury. Additionally, the context can be influenced by user feedback or historical data that suggests patterns or risks associated with similar activities, such that the processing circuits can determine why the user is seeking anatomical improvements and tailor the protocol accordingly.

In some implementations, the anatomical conditioning protocol including the plurality of anatomy exercises can include a targeted rehabilitation (e.g., knee recovery, shoulder strengthening, back pain relief) or targeted strength development (e.g., core stability, muscle building) of the one or more regions, muscles, ligaments, or tendons of the anatomy of the user. That is, the processing circuits can generate a rehabilitation plan based on specific weaknesses detected during testing and modeling. For example, a targeted rehabilitation can be focused on rebuilding strength after a torn ligament. In this example, the anatomy exercises of the anatomical conditioning protocol can include low-impact resistance training. In another example, a targeted strength development can be focused on improving overall athletic performance. In this example, the anatomy exercises of the anatomical conditioning protocol can include strength-building exercises focused on high-intensity interval training.

In some implementations, method 200 can further include the processing circuits generating at least one updated anatomy score based at least on applying one or more updated results of performance of the at least one mobility test or the at least one muscle, ligament, or tendon test, the anatomy information, and the objective or an updated objective of the anatomy of the user as input to the at least one second neural network. That is, the processing circuits can generate updated scores as the user progresses through the conditioning protocol. The scores can be generated using the neural networks. For example, the second neural network can receive the latest performance data (e.g., joint angles, muscle force measurements, and range of motion data) as input, and process the data through a series of hidden layers trained to correlate these metrics with anatomical performance indicators. The neural network can then apply weights and biases learned from the training data to generate updated anatomy scores, refining predictions based on the ongoing performance of the user.

In some implementations, the generating can be responsive to a predetermined schedule (e.g., after a set number of weeks, upon completion of a particular set of exercises). That is, the predetermined schedule can be a specific time interval (e.g., four weeks, six weeks), completion of a set number of exercise sessions (e.g., 10 sessions, 20 sessions), or based on performance milestones (e.g., achieving a targeted joint stability score, reaching a certain range of motion). The input to the second neural network can cause the at least one second neural network to generate the at least one updated anatomy score corresponding with the anatomy of the user. That is, the processing circuits can update the profile of the user with new data and refine the conditioning protocol accordingly. For example, the updated anatomy score can indicate improved joint stability, which can lead to an adjustment in the intensity or focus of the conditioning plan by recalculating the optimal weights, repetitions, or range of motion targets. In another example, the updated anatomy score can indicate no improvement, prompting the processing circuits to re-evaluate the current protocol and recommend alternative exercises. That is, re-evaluation by the neural networks can include analyzing the detailed subscore data of user (e.g., region-specific scores for the knees, hips, or shoulders) and identifying which areas show stagnation or regression, thereby triggering an update in the exercise plan to address the specific underperforming regions.

Figure 3:
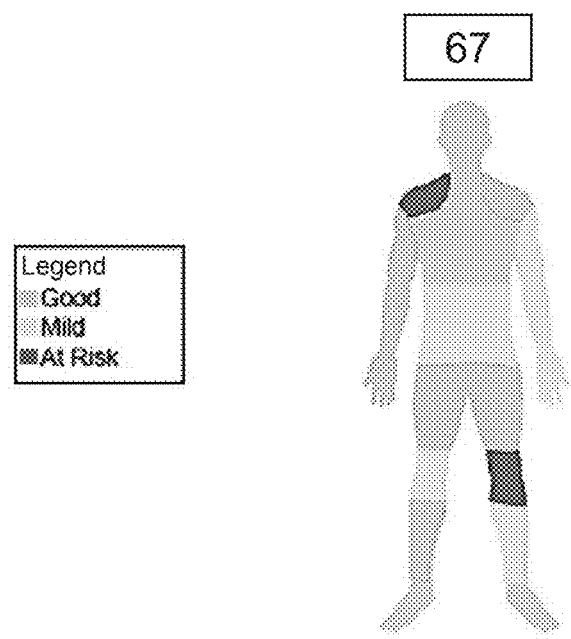
FIG. 3 depicts an example graphical user interface, in accordance with some implementations of the present disclosure.

Referring now to FIG. 3, depicting an example graphical user interface, in accordance with some implementations of the present disclosure. That is, the application 142 of the user device 140 of FIG. 1 can be configured to present a patient output display. The application 142 can retrieve data from the model system 110, including anatomy information such as name, date of test, age, height, weight, and BMI, and present this data on the graphical user interface. The data can be processed by the application 142 after being transmitted through the network 130 and stored in the user data 124 of the model database 120. The test results, such as mobility, muscle strength, and broad jump performance, can be presented in a comparative format, where the results of the user are displayed in relation to, for example, peers in the same age group. The mobility test results (e.g., average), muscle test results (e.g., below average), and broad jump results (e.g., above average) can be processed by the model system 110 and displayed by application 142 to facilitate interpretation. In some implementations, the application 142 can also display an overall biomechanical optimum output score (e.g., 67 in this case), which can be generated by the model system 110 based on the performance of the user across multiple tests. For example, the score can be an aggregated output calculated by the neural network of modeler 114, which receives input from various tests and generates an assessment of the biomechanical condition of the user.

Additionally, FIG. 3 depicts a graphical outline of the body of user, where specific regions are shaded (or otherwise shown) to indicate areas of concern. The visualization can be generated by the application 142 of the user device 140, receiving anatomy subscores from the model system 110. For example, the subscores can be categorized into "good,"

"mild," or "at risk," as indicated by the shading of the body parts in the figure (e.g., the left shoulder and right knee are marked as "at risk"). The subscores can be derived from individual test results processed by neural networks within the modeler 114 of the model system 110. The application 142 can facilitate the identification of key regions that require attention, such as areas of instability, weakness, or limited mobility. The subscores can be generated based on the performance of the user in muscle, ligament, and mobility tests, with predefined thresholds stored in the training dataset 122. As seen in FIG. 3, the corresponding color-coded regions provide insight into the physical condition of the user. This information can be used to generate personalized anatomical conditioning protocols by the second neural network, which can outputs a set of exercises to the application 142. In this example, regions marked as "at risk" can trigger specific exercises focused on improving those areas. The application 142 can integrate the test data of the user and subscores to create a user-centric exercise regimen for preventing injury or enhancing performance.

In some implementations, the model system 110 of FIG. 1 can generate a GUI including an anatomical outline of the anatomy of the user. This anatomical outline, as seen in FIG. 3, can include at least one indicator corresponding to one of the plurality of regions or portions of the anatomy of the user. The indicators can be visualized on the body outline, where distinct regions (e.g., left shoulder, right knee) can be highlighted based on anatomy subscores generated by the model system 110. The subscores can represent a quantitative assessment of the condition of the user in various anatomical regions, based on the test results (e.g., mobility tests, muscle tests). The GUI can allow the users and professionals (e.g., doctors, trainers, or other third-parties) to assess which areas of the body are in good condition, mildly impacted, or at risk. In the example shown in FIG. 3, the left knee and right shoulder are marked as "at risk" based on subscores generated by the model system 110. These subscores can predict a future condition of the corresponding body part based on historical performance data, biomechanical patterns, and thresholds used to categorize the condition (e.g., good, mild, at-risk). The GUI can provide a visual summary that helps identify regions requiring further attention or intervention.

The model system 110 can further provide the GUI including the anatomy score, the plurality of anatomy subscores, and the corresponding indicators for each anatomical region or portion of the body. In FIG. 3, each subscore can correspond to a specific region, such as the right knee or left shoulder, and each region can be categorized into one of three conditions based on the subscore: a first category representing a favorable condition, a second category representing a mild condition, and a third category representing an at-risk condition. For example, in FIG. 3, the left knee and right shoulder are categorized as "at-risk" (represented in darker shading), while the remainder of the body is categorized as either "good" or "mild." These classifications can be derived from the subscores generated by the neural network within the modeler 114, which processes the results of mobility, muscle, and ligament tests.

Figure 4:
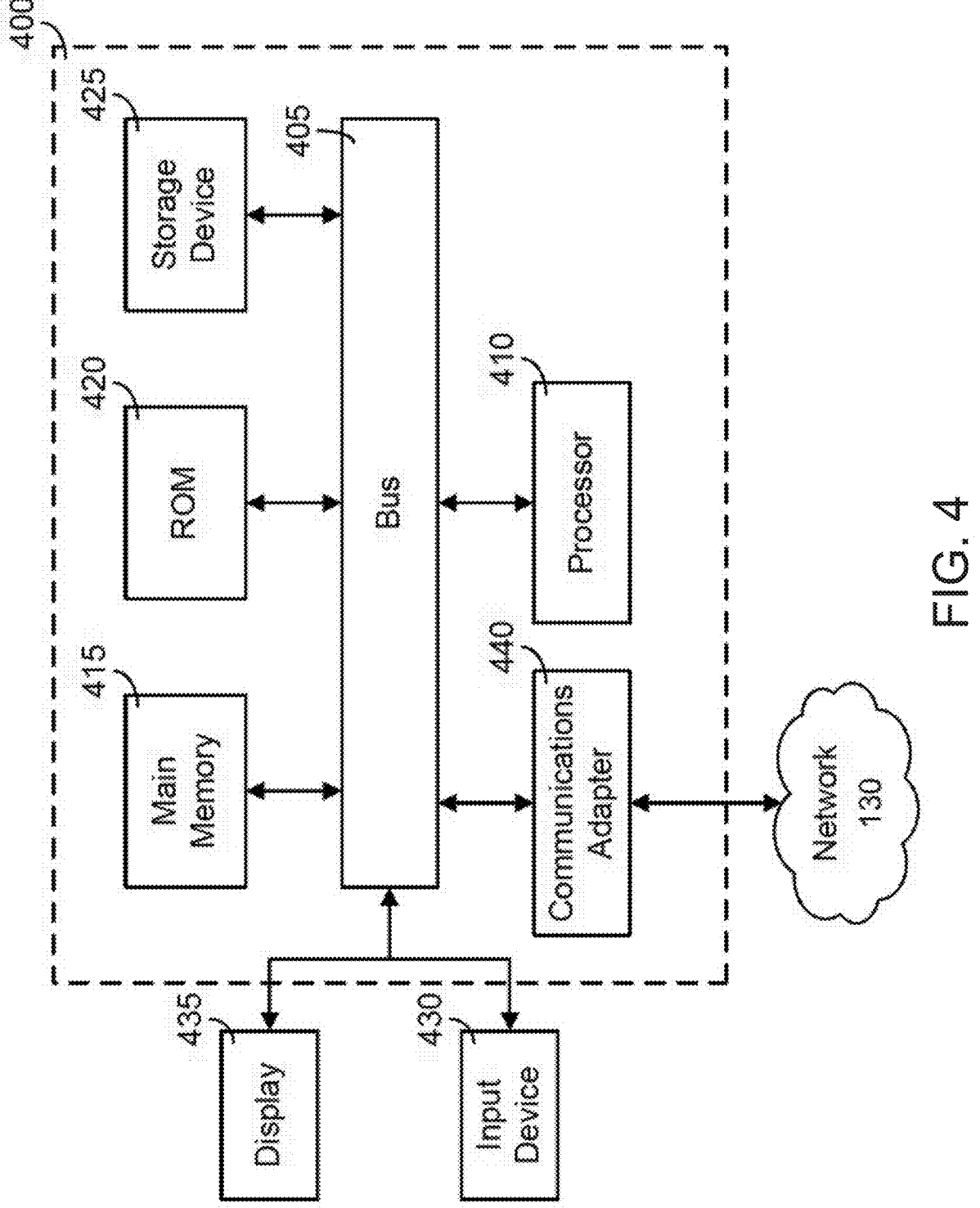
FIG. 4 is a block diagram illustrating an example computing system suitable for use in the various implementations described herein.

FIG. 4 illustrates a depiction of a computing system 400 that can be used, for example, to implement an example model system 110, an example user device 140, an example sensor device 150, and/or various other illustrative systems described in the present disclosure. The computing system 400 includes a bus 405 or other communication component for communicating information and a processor 410 coupled to the bus 405 for processing information. The computing system 400 also includes main memory 415, such as a random-access memory (RAM) or other dynamic storage device, coupled to the bus 405 for storing information, and instructions to be executed by the processor 410. Main memory 415 can also be used for storing position information, temporary variables, or other intermediate information during execution of instructions by the processor 410. The computing system 400 can further include a read only memory (ROM) 420 or other static storage device coupled to the bus 405 for storing static information and instructions for the processor 410. A storage device 425, such as a solid-state device, cloud storage, third-party storage, magnetic disk or optical disk, is coupled to the bus 405 for persistently storing information and instructions.

The computing system 400 can be coupled via the bus 405 to a display 435, such as a liquid crystal display, or active matrix display, for displaying information to a user. An input device 430, such as a keyboard including alphanumeric and other keys, can be coupled to the bus 405 for communicating information, and command selections to the processor 410. In another implementation, the input device 430 has a touch screen display 435. The input device 430 can include a cursor control, such as a mouse, a trackball, or cursor direction keys, for communicating direction information and command selections to the processor 410 and for controlling cursor movement on the display 435.

In some implementations, the computing system 400 can include a communications adapter 440, such as a networking adapter. Communications adapter 440 can be coupled to bus 405 and can be configured to facilitate communications with a computing or communications network 130 and/or other computing systems. In various illustrative implementations, any type of networking configuration can be achieved using communications adapter 440, such as wired (e.g., via Ethernet), wireless (e.g., via Wi-Fi, Bluetooth, etc.), pre-configured, ad-hoc, LAN, WAN, etc.

According to various implementations, the processes that effectuate illustrative implementations that are described herein can be achieved by the computing system 400 in response to the processor 410 executing an arrangement of instructions contained in main memory 415. Such instructions can be read into main memory 415 from another computer-readable medium, such as the storage device 425. Execution of the arrangement of instructions contained in main memory 415 causes the computing system 400 to perform the illustrative processes described herein. One or more processors in a multi-processing arrangement can also be employed to execute the instructions contained in main memory 415. In alternative implementations, hard-wired circuitry can be used in place of or in combination with software instructions to implement illustrative implementations. Thus, implementations are not limited to any specific combination of hardware circuitry and software.

Although an example processing system has been described in FIG. 4, implementations of the subject matter and the functional operations described in this specification can be carried out using other types of digital electronic circuitry, or in computer software, firmware, or hardware, including the structures disclosed in this specification and their structural equivalents, or in combinations of one or more of them.

FIG. 5A illustrates an example mobility test (e.g., hip flexor), in accordance with some implementations of the present disclosure. The first depiction 500 depicts a user lying on their back with one knee drawn towards the chest, while the other leg remains extended on the surface, for example parallel to a straight horizontal device (e.g., PVC pipe). In this example, multimedia data, such as video footage, can be collected from a camera or sensor device positioned to capture the movement and posture of the user. The processing circuits can collect this data in real time as the user performs the test. In the second depiction 510, the user alternates the leg being held towards the chest. The collected multimedia data can be applied as input to at least one first neural network, which can process the data to assess range of motion and alignment of the hip, knee, and lower back of the user based at least on the position of the leg relative to the other parts of the body (e.g., hip, knee, back) and/or the parallel measuring device. In some implementations, the neural network can generate results indicating whether the mobility of the user meets and/or satisfies predefined thresholds for hip flexion and/or any compensatory movements or limitations in range of motion. For example, the results can be used to establish a baseline for hip and lower body flexibility.

Figure 5B:
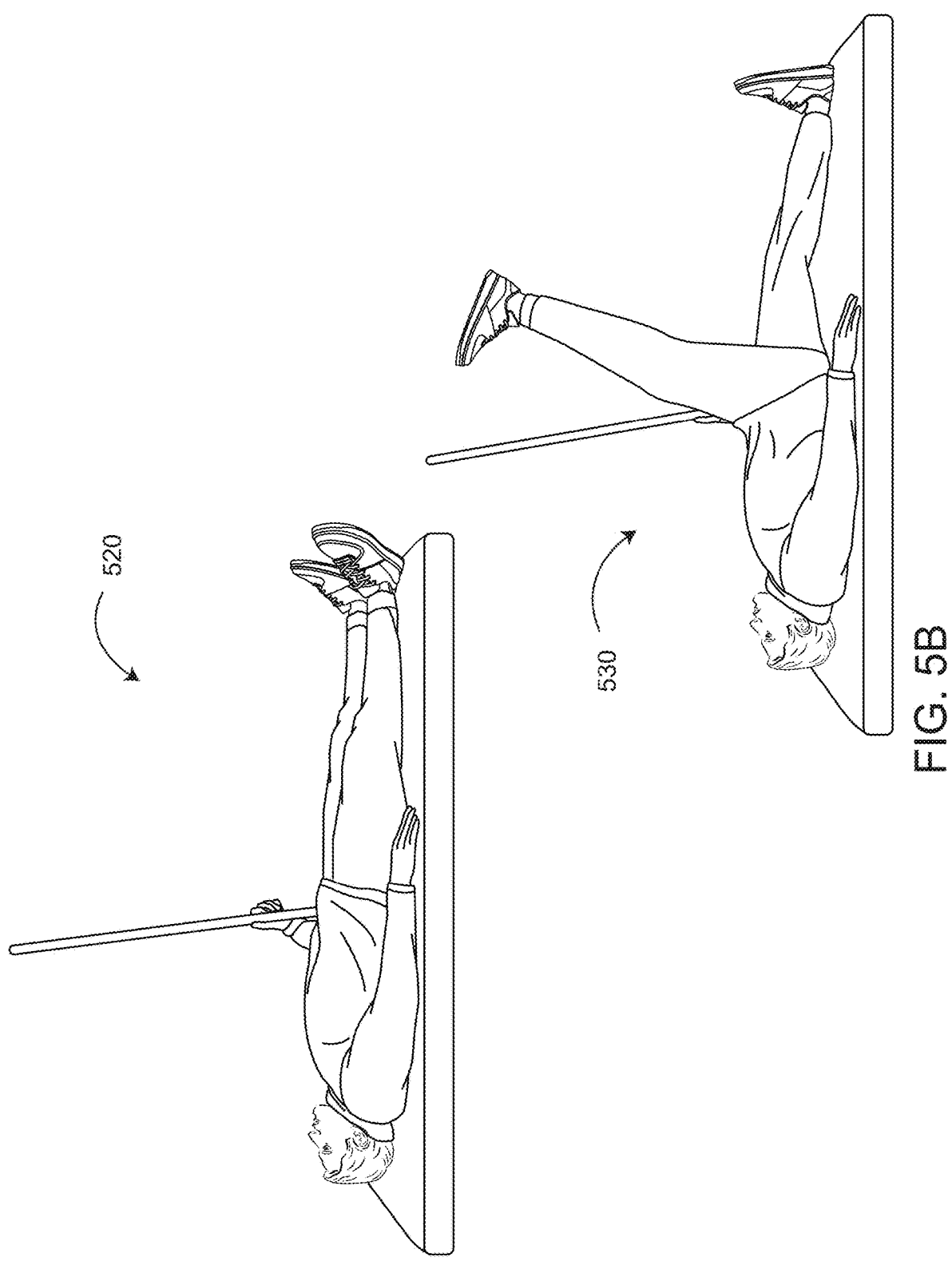

FIG. 5B illustrates an example flexibility assessment (e.g., hamstring) involving leg movement, in accordance with some implementations of the present disclosure. The initial depiction 520 depicts the user lying on their back with a neutral leg position while holding a stick vertically. In the second depiction 530, the user lifts one leg upwards, aiming for a straight, aligned movement. The processing circuits can collect multimedia or sensor data from this movement sequence, using a camera or sensor device positioned to capture the movement trajectory of the leg, relative to the other body parts of a user (e.g., hip, knee, back) and/or the measuring device (e.g., stick). For example, the data can be input into a neural network, which can process the motion for attributes such as knee extension, hip alignment, and/or overall flexibility. The neural network can generate a first result indicating the range of motion achieved by the leg and identify any asymmetries or compensations that can suggest tightness or weakness in the hamstring or hip flexors.

FIG. 5C illustrates an example stability test (e.g., ankle) focused on ankle and calf strength, in accordance with some implementations of the present disclosure. In the initial depiction 540, the user stands facing a wall with their hands placed against it and their knees slightly bent. In the second depiction 550, the user flexes the knees further, shifting their weight forward. The processing circuits can capture multimedia data from this movement using a camera or sensor positioned to record the ankle alignment and knee movement of the user. The collected data can be applied to at least one first neural network that models the stability of the ankle and lower leg, analyzing metrics such as angle deviations and muscle activation patterns. The neural network can generate a result that indicates whether the ankle stability of the user falls within acceptable limits (e.g., identifying imbalances or weaknesses that could predispose the user to injury).

The herein described subject matter sometimes illustrates different components contained within, or connected with, different other components. It is to be understood that such depicted architectures are illustrative, and that in fact many other architectures can be implemented which achieve the same functionality. In a conceptual sense, any implementation of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations can be expressly set forth herein for sake of clarity. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description can illustrate a specific order of method steps, the order of such steps can differ from what is depicted and described, unless specified differently above. Also, two or more steps can be performed concurrently or with partial concurrence, unless specified differently above. Such variation can depend, for example, on the software and hardware systems chosen and on designer choice. All such variations are within the scope of the disclosure. Likewise, software implementations of the described methods can be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to disclosures containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent. The foregoing description of illustrative implementations has been presented for purposes of illustration and of description. It is not intended to be exhaustive or limiting with respect to the precise form disclosed, and modifications and variations are possible in light of the above teachings or can be acquired from practice of the disclosed implementations. It is intended that the scope of the disclosure be defined by the claims appended hereto and their equivalents.

What is claimed is:

1. A method, comprising:

receiving, by one or more processing circuits, a request comprising anatomy information of a user and an objective of an anatomy of the user;

determining or identifying, by the one or more processing circuits, a plurality of anatomical tests to perform by the user;

collecting, by the one or more processing circuits from at least one camera or at least one first sensor, a set of images or videos of a performance of at least one mobility test of the plurality of anatomical tests performed by the user;

applying, by the one or more processing circuits, the set of images or videos as input to at least one first neural network to cause the at least one first neural network to generate at least one first result of the at least one mobility test, wherein the at least one first neural network comprises a vision model, the set of multimedia or the first sensor data images or videos is applied to an input layer of the vision model to model the performance of the user to generate, in an output layer, the at least one first result of the plurality of anatomical tests based at least on detecting and mapping one or more anatomical landmarks of the user in the set of images or videos to one or more predefined mobility thresholds, wherein the vision model tracks the one or more anatomical landmarks of the user in the set of images and videos;

collecting, by the one or more processing circuits from at least one second sensor, second sensor data during performance of at least one muscle, ligament, or tendon test of the plurality of anatomical tests performed by the user;

determining, by the one or more processing circuits, at least one second result of the at least one muscle, ligament, or tendon test based at least on a predetermined threshold;

applying, by the one or more processing circuits, the at least one first result of the performance of the at least one mobility test, the at least one second result of the performance of the at least one muscle, ligament, or tendon test, the anatomy information, and objective of the anatomy of the user as input to at least one second neural network to cause the at least one second neural network to generate (i) at least one anatomy score corresponding with the anatomy of the user and a plurality of anatomy subscores corresponding to one or more regions or portions of the anatomy of the user, and (ii) an anatomical conditioning protocol comprising at least a plurality of anatomy exercises based at least on the objective of the anatomy of the user and the plurality of anatomy subscores corresponding to the one or more regions or portions of the anatomy of the user, wherein the at least one second neural network is configured based on at least one physical profile of a plurality of different users;

providing, by the one or more processing circuits, the at least one anatomy score and the anatomical conditioning protocol;

monitoring, by the one or more processing circuits, a progress of the anatomical conditioning protocol based at least on receiving an indication of a performance by the user, the indication comprising at least one of:

receiving application data of a user device of the user or a third-party;

receiving, via an interface, an input from the user or the third-party; or receiving an input from a sensor device positioned to monitor the user or coupled to the user; and updating, by the one or more processing circuits, the at least one anatomy score and at least one of the plurality of anatomy subscores based on the progress.

2. The method of claim 1, further comprising:

monitoring, by the one or more processing circuits, the progress of the anatomical conditioning protocol further based on comparing the indication of the performance with at least one of the plurality of anatomy exercises.

3. The method of claim 1, further comprising:

generating, by the one or more processing circuits, a graphical user interface (GUI) comprising an anatomical outline of the anatomy of the user, wherein the anatomical outline comprises at least one indicator corresponding at least one of a plurality of regions or portions of the anatomy of the user, and wherein the at least one indicator represents a prediction of a future condition of at least one of the plurality of regions or portions of the anatomy of the user based at least on a corresponding anatomy subscore of the plurality of anatomy subscores; and providing, by the one or more processing circuits, the GUI comprising the at least one indicator, the at least one anatomy score, and the plurality of anatomy subscores, each of the plurality of anatomy subscores corresponding to at least one of the plurality of regions or portions of the anatomy of the user, wherein the at least one indicator categorizes each of the plurality of regions or portions into a first category representing a favorable condition, a second category representing a mild condition, and a third category representing an at-risk condition based at least on the corresponding anatomy subscore.

4. The method of claim 1, wherein the anatomical conditioning protocol comprises an exercise or recovery routine corresponding with a frequency and duration of at least one of the plurality of anatomy exercises, wherein the method further comprises:

receiving, by the one or more processing circuits, performance data of the user; and updating, by the one or more processing circuits, the exercise or recovery routine based at least on the performance data.

5. The method of claim 1, further comprising:

generating, by the one or more processing circuits, a prompt based on at least the anatomy information, the at least one first result of the at least one mobility test, and the at least one second result of the at least one muscle, ligament, or tendon test, wherein generating the prompt comprises identifying one or more anatomical conditions of the user and the objective of the anatomy of the user.

6. The method of claim 1, further comprising:

identifying, by the one or more processing circuits, a context based at least on the objective of the anatomy of the user, wherein the context corresponds to one or more regions, muscles, ligaments, or tendons of the anatomy of the user, and wherein the anatomical conditioning protocol comprising the plurality of anatomy exercises comprise a targeted rehabilitation or targeted development of the one or more regions, muscles, ligaments, or tendons of the anatomy of the user.

7. The method of claim 1, wherein the at least one first neural network is applied to the set of images or videos to analyze the at least one mobility test based at least on:

comparing a range of motion in the set of images or videos to the one or more predefined mobility thresholds; and determining the at least one first result of the at least one mobility test based on the user meeting or exceeding the one or more predefined mobility thresholds.

8. The method of claim 1, wherein determining the at least one second result of the at least one muscle, ligament, or tendon test comprises aggregating and averaging a plurality of muscle, ligament, or tendon tests of at least one muscle, ligament, or tendon of the user, and wherein the second sensor data comprises one or more force measurements from the at least one second sensor positioned to monitor at least one muscle, ligament, or tendon corresponding with the at least one muscle, ligament, or tendon test.

9. The method of claim 1, further comprising:

responsive to a predetermined schedule, generating, by the one or more processing circuits, at least one updated anatomy score based at least on applying one or more updated results of performance of the at least one mobility test or the at least one muscle, ligament, or tendon test, the anatomy information, and the objective or an updated objective of the anatomy of the user as input to the at least one second neural network to cause the at least one second neural network to generate the at least one updated anatomy score corresponding with the anatomy of the user.

10. A system, comprising:

one or more processing circuits configured to:

receive a request comprising anatomy information of a user and an objective of an anatomy of the user;

determine or identify a plurality of anatomical tests to perform by the user;

collect, from at least one camera or at least one first sensor, a set of images or videos of a performance of at least one mobility test of the plurality of anatomical tests performed by the user;

generate, using a vision model, at least one first result of the at least one mobility test based on the set of images or videos, wherein the set of images or videos is applied to an input layer of the vision model to model the performance of the user to generate, in an output layer, the at least one first result of the plurality of anatomical tests based at least on detecting and mapping one or more anatomical landmarks of the user in the set of images or videos to one or more predefined mobility thresholds, wherein the vision model tracks the one or more anatomical landmarks of the user in the set of images and videos;

collect, from at least one second sensor, second sensor data during performance of at least one muscle, ligament, or tendon test of the plurality of anatomical tests performed by the user;

determine at least one second result of the at least one muscle, ligament, or tendon test based at least on a predetermined threshold;

apply the at least one first result of the performance of the at least one mobility test, the at least one second result of the performance of the at least one muscle, ligament, or tendon test, the anatomy information, and objective of the anatomy of the user as input to at least one neural network to cause the at least one neural network to generate (i) at least one anatomy score corresponding with the anatomy of the user and a plurality of anatomy subscores corresponding to one or more regions or portions of the anatomy of the user, and (ii) an anatomical conditioning protocol comprising at least a plurality of anatomy exercises based at least on the objective of the anatomy of the user and the plurality of anatomy subscores corresponding to the one or more regions or portions of the anatomy of the user, wherein the at least one neural network is configured based on at least one physical profile of a plurality of different users;

provide the at least one anatomy score and the anatomical conditioning protocol;

monitor a progress of the anatomical conditioning protocol based at least on receiving an indication of a performance by the user, the indication comprising at least one of:

receiving application data of a user device of the user or a third-party;

receiving, via an interface, an input from the user or the third-party; or receiving an input from a sensor device positioned to monitor the user or coupled to the user; and update the at least one anatomy score and at least one of the plurality of anatomy subscores based on the progress.

11. The system of claim 10, the one or more processing circuits are further configured to:

monitor the progress of the anatomical conditioning protocol further based on comparing the indication of the performance with at least one of the plurality of anatomy exercises.

12. The system of claim 10, the one or more processing circuits are further configured to:

generate a graphical user interface (GUI) comprising an anatomical outline of the anatomy of the user, wherein the anatomical outline comprises at least one indicator corresponding at least one of a plurality of regions or portions of the anatomy of the user, and wherein the at least one indicator represents a prediction of a future condition of at least one of the plurality of regions or portions of the anatomy of the user based at least on a corresponding anatomy subscore of the plurality of anatomy subscores; and provide the GUI comprising the at least one indicator, the at least one anatomy score, and the plurality of anatomy subscores, each of the plurality of anatomy subscores corresponding to at least one of the plurality of regions or portions of the anatomy of the user, wherein the at least one indicator categorizes each of the plurality of regions or portions into a first category representing a favorable condition, a second category representing a mild condition, and a third category representing an at-risk condition based at least on the corresponding anatomy subscore.

13. The system of claim 10, wherein the anatomical conditioning protocol comprises an exercise or recovery routine corresponding with a frequency and duration of at least one of the plurality of anatomy exercises, wherein the one or more processing circuits are further configured to:

receive performance data of the user; and update the exercise or recovery routine based at least on the performance data.

14. The system of claim 10, the one or more processing circuits are further configured to:

generate a prompt based on at least the anatomy information, the at least one first result of the at least one mobility test, and the at least one second result of the at least one muscle, ligament, or tendon test, wherein generating the prompt comprises identifying one or more anatomical conditions of the user and the objective of the anatomy of the user.

15. The system of claim 10, the one or more processing circuits are further configured to:

identify a context based at least on the objective of the anatomy of the user, wherein the context corresponds to one or more regions, muscles, ligaments, or tendons of the anatomy of the user, and wherein the anatomical conditioning protocol comprising the plurality of anatomy exercises comprise a targeted rehabilitation or targeted development of the one or more regions, muscles, ligaments, or tendons of the anatomy of the user.

16. A non-transitory computer readable medium including one or more instructions stored thereon, and when the one or more instructions are executed by at least one processor causes the at least one processor to execute operations of:

applying a set of images or videos as input to at least one first neural network to cause the at least one first neural network to generate at least one first result of at least one mobility test, wherein the at least one first neural network comprises a vision model, the set of images or videos is applied to an input layer of the vision model to model a performance of a user to generate, in an output layer, the at least one first result of a plurality of anatomical tests based at least on detecting and mapping one or more anatomical landmarks of the user in the set of images or videos to one or more predefined mobility thresholds, wherein the vision model tracks the one or more anatomical landmarks of the user in the set of images and videos;

applying the at least one first result of the performance of the at least one mobility test, anatomy information, and objective of an anatomy of the user as input to at least one second neural network to cause the at least one second neural network to generate (i) at least one anatomy score corresponding with the anatomy of the user and a plurality of anatomy subscores corresponding to one or more regions or portions of the anatomy of the user, and (ii) an anatomical conditioning protocol comprising at least a plurality of anatomy exercises based at least on then objective of the anatomy of the user and the plurality of anatomy subscores corresponding to the one or more regions or portions of the anatomy of the user, wherein the at least one second neural network is configured based on at least one physical profile of a plurality of different users;

providing the at least one anatomy score and the anatomical conditioning protocol;

monitoring a progress of the anatomical conditioning protocol based at least on receiving an indication of a performance by the user, the indication comprising at least one of:

receiving application data of a user device of the user or a third-party;

receiving, via an interface, an input from the user or the third-party; or receiving an input from a sensor device positioned to monitor the user or coupled to the user; and updating the at least one anatomy score and at least one of the plurality of anatomy subscores based on the progress.

* * * * *